US008972106B2

(12) United States Patent
Prakah-Asante et al.

(10) Patent No.: US 8,972,106 B2
(45) Date of Patent: Mar. 3, 2015

(54) SYSTEMS AND METHODS FOR SCHEDULING DRIVER INTERFACE TASKS BASED ON DRIVER WORKLOAD

(71) Applicant: Ford Global Technologies, LLC, Dearborn, MI (US)

(72) Inventors: Kwaku O. Prakah-Asante, Commerce Township, MI (US); Jialiang Le, Canton, MI (US); Manoharprasad K. Rao, Novi, MI (US); Gary Steven Strumolo, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 14/045,895

(22) Filed: Oct. 4, 2013

(65) Prior Publication Data
US 2014/0039757 A1 Feb. 6, 2014

Related U.S. Application Data

(63) Continuation-in-part of application No. 13/809,038, filed as application No. PCT/US2010/043605 on Jul. 29, 2010.

(51) Int. Cl.
*G06F 7/00* (2006.01)
(52) U.S. Cl.
CPC .......................................... *G06F 7/00* (2013.01)
USPC .......................................................... 701/36
(58) Field of Classification Search
None
See application file for complete search history.

(56) References Cited

U.S. PATENT DOCUMENTS

| 6,502,022 B1 | 12/2002 | Chastain et al. |
| 6,580,984 B2 | 6/2003 | Fecher et al. |
| 6,661,345 B1 * | 12/2003 | Bevan et al. ................... 340/575 |
| 6,683,881 B1 | 1/2004 | Mijares et al. |
| 6,873,911 B2 | 3/2005 | Nishira et al. |
| 6,892,116 B2 | 5/2005 | Geisler et al. |
| 6,925,425 B2 * | 8/2005 | Remboski et al. ............ 702/188 |
| 6,988,056 B2 | 1/2006 | Cook |
| 6,995,663 B2 | 2/2006 | Geisler et al. |

(Continued)

FOREIGN PATENT DOCUMENTS

| EP | 1512374 | 3/2005 |
| EP | 1512584 | 3/2005 |

(Continued)

OTHER PUBLICATIONS

International Search Report and Written Opinion for International Application No. PCT/US10/43605, Sep. 23, 2010.

(Continued)

*Primary Examiner* — Thomas Tarcza
*Assistant Examiner* — Adam Alharbi
(74) *Attorney, Agent, or Firm* — Jennifer M. Stec; Brooks Kushman P.C.

(57) ABSTRACT

A vehicle's dynamic handling state, driver inputs to the vehicle, driver physiological condition, etc. may be examined to determine one or more measures of driver workload. Driver interface tasks may then be delayed and/or prevented from executing based on the driver workload so as to not increase the driver workload. Alternatively, driver interface tasks may be schedule for execution based on the driver workload and caused to execute according to the schedule, for example, to minimize the impact the executing driver interface tasks have on driver workload.

18 Claims, 17 Drawing Sheets

(56) References Cited

U.S. PATENT DOCUMENTS

| | | | |
|---|---|---|---|
| 6,998,972 B2 | 2/2006 | Geisler et al. | |
| 7,216,022 B2 | 5/2007 | Kynast et al. | |
| 7,253,724 B2 | 8/2007 | Prakah-Asante et al. | |
| 7,292,152 B2 | 11/2007 | Torkkola et al. | |
| 7,349,782 B2 | 3/2008 | Churchill et al. | |
| 7,365,651 B2 | 4/2008 | Massey et al. | |
| 7,532,958 B2 | 5/2009 | Powers et al. | |
| 7,610,130 B1 | 10/2009 | Dixon et al. | |
| 7,616,129 B2 | 11/2009 | Thacher | |
| 8,117,367 B2 | 2/2012 | Conti et al. | |
| 8,417,415 B2 | 4/2013 | Phelan | |
| 2002/0091473 A1 | 7/2002 | Gardner et al. | |
| 2002/0120374 A1* | 8/2002 | Douros et al. | 701/29 |
| 2002/0121981 A1 | 9/2002 | Munch | |
| 2004/0153707 A1 | 8/2004 | Ellerbrock et al. | |
| 2004/0181334 A1 | 9/2004 | Blumbergs et al. | |
| 2004/0252027 A1* | 12/2004 | Torkkola et al. | 340/576 |
| 2005/0204057 A1 | 9/2005 | Anderson et al. | |
| 2006/0064215 A1 | 3/2006 | Turski et al. | |
| 2006/0071981 A1 | 4/2006 | Plunkett | |
| 2006/0122741 A1 | 6/2006 | Bassiere et al. | |
| 2006/0190822 A1 | 8/2006 | Basson et al. | |
| 2006/0287787 A1 | 12/2006 | Engstrom et al. | |
| 2007/0006150 A9 | 1/2007 | Walmsley | |
| 2007/0126604 A1 | 6/2007 | Thacher | |
| 2008/0154438 A1 | 6/2008 | Kalik | |
| 2009/0040054 A1 | 2/2009 | Wang et al. | |
| 2011/0081955 A1 | 4/2011 | Lange et al. | |
| 2011/0173363 A1 | 7/2011 | Conti et al. | |
| 2011/0195699 A1 | 8/2011 | Tadayon et al. | |
| 2011/0263383 A1 | 10/2011 | Ostberg et al. | |
| 2011/0298279 A1 | 12/2011 | Dimrco et al. | |
| 2012/0188376 A1 | 7/2012 | Chatow et al. | |
| 2013/0066688 A1 | 3/2013 | Pinkus | |

FOREIGN PATENT DOCUMENTS

| | | |
|---|---|---|
| EP | 1513326 | 3/2005 |
| JP | 08201235 | 8/1996 |
| JP | 09086378 | 3/1997 |
| JP | 09329458 | 12/1997 |
| JP | 10338120 | 12/1998 |
| JP | 2001354047 | 12/2001 |
| JP | 2004524203 A | 8/2004 |
| JP | 2004312055 | 11/2004 |
| JP | 2005070057 | 3/2005 |
| JP | 2006343904 | 12/2006 |
| JP | 2007511414 A | 5/2007 |
| JP | 2007230422 A | 9/2007 |
| JP | 2007261432 | 10/2007 |
| JP | 2008149857 A | 7/2008 |
| WO | 2010051414 A1 | 5/2010 |
| WO | 2010051428 A1 | 5/2010 |
| WO | 2010062671 A1 | 6/2010 |

OTHER PUBLICATIONS

The All-New Volvo S40: IDIS Helps The Driver Avoid Distractions In Busy Situations, Press Release, Oct. 19, 2003, https://www.media.volvocars.com/global/en-gb/media/pressreleases/4908, 3 pgs.

* cited by examiner

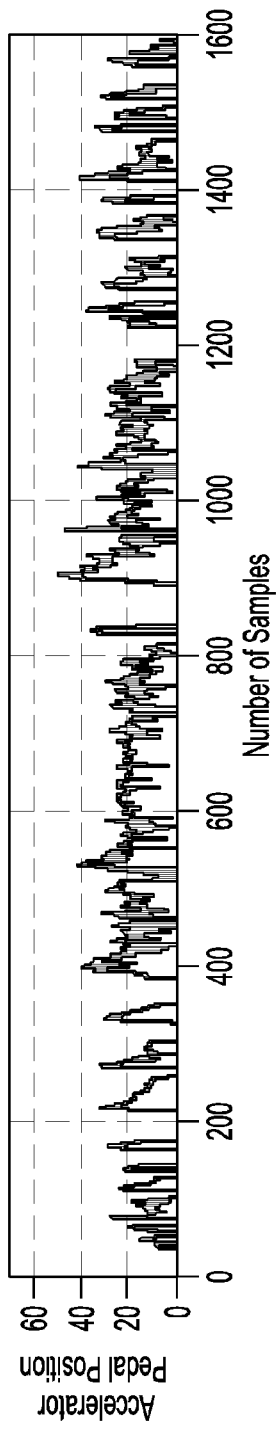
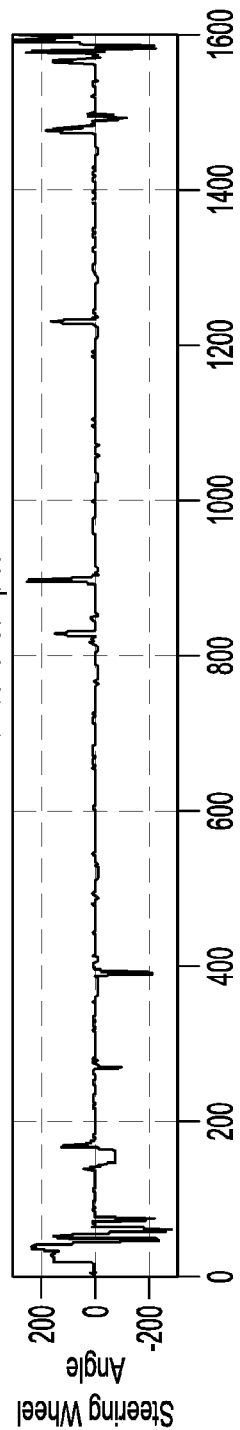
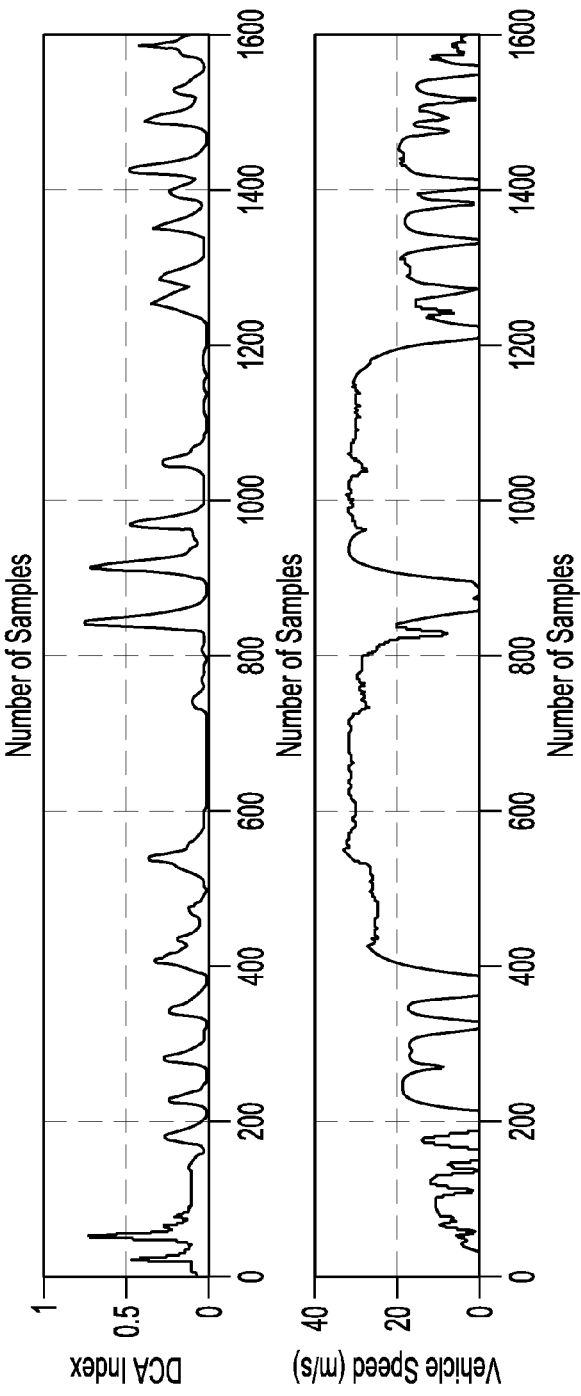
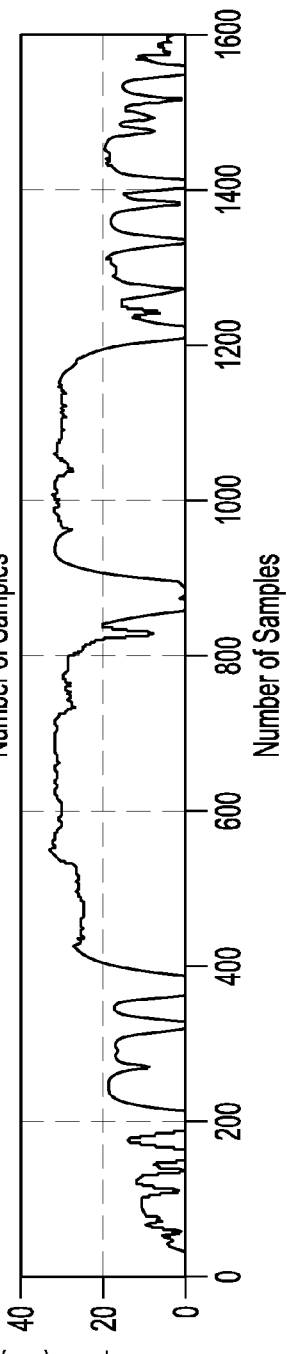
Fig-15A
Fig-15B
Fig-15C
Fig-15D

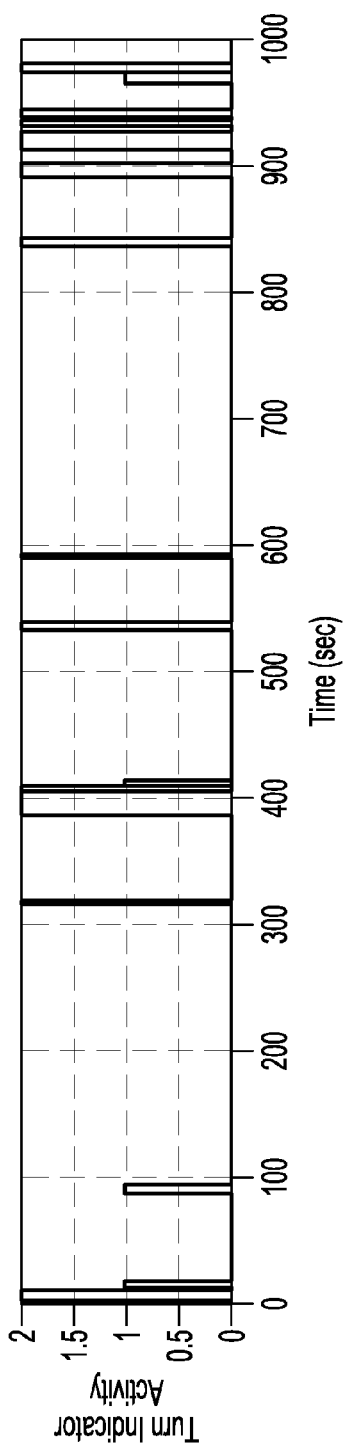
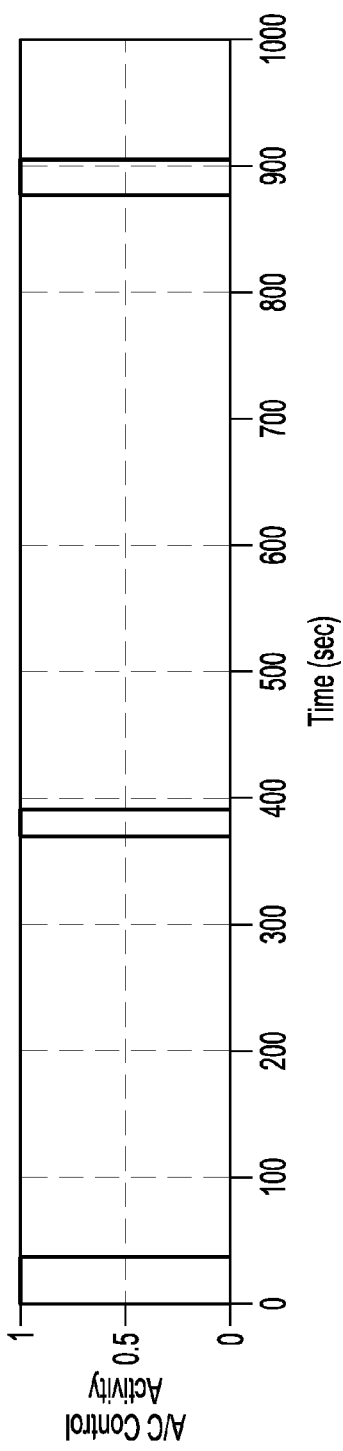
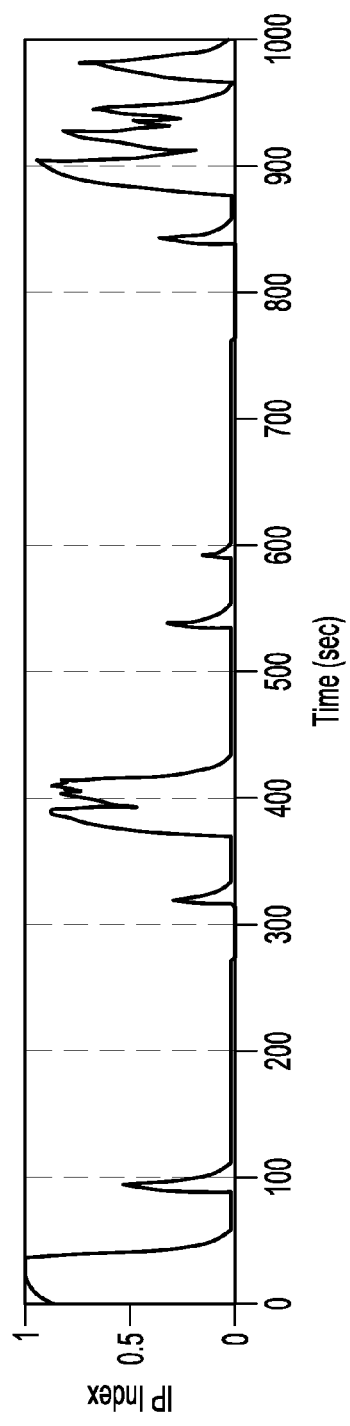

SYSTEMS AND METHODS FOR SCHEDULING DRIVER INTERFACE TASKS BASED ON DRIVER WORKLOAD

CROSS-REFERENCE TO RELATED APPLICATIONS

This application is a continuation-in-part of application Ser. No. 13/809,038, filed Jan. 8, 2013, which is the National Stage of International Application No. PCT/US10/43605, filed Jul. 29, 2010, the disclosures of each of which are incorporated in their entirety by reference herein.

BACKGROUND

Certain vehicles may provide infotainment information, navigation information, etc. to enhance the driving experience. As the interaction between drivers and these vehicles increases, it may be beneficial to facilitate such interaction without increasing driver workload.

SUMMARY

Measures of driver workload may be determined from vehicle, driver and/or environmental information. Certain driver interface tasks may be selectively delayed or prevented from executing based on the determined driver workload. Alternatively, driver interface tasks may be scheduled for execution based on the determined driver workload and then caused to execute according to the schedule.

BRIEF DESCRIPTION OF THE DRAWINGS

FIGS. 15A through 15D are example plots of accelerator pedal position, steering wheel angle, Driver Control Action (DCA) Index, and vehicle speed respectively.

FIGS. 16A through 16C are example plots of turn indicator activity, air conditioning control activity, and Instrument Panel (IP) Index respectively.

DETAILED DESCRIPTION

I. Introduction

Figure 1:
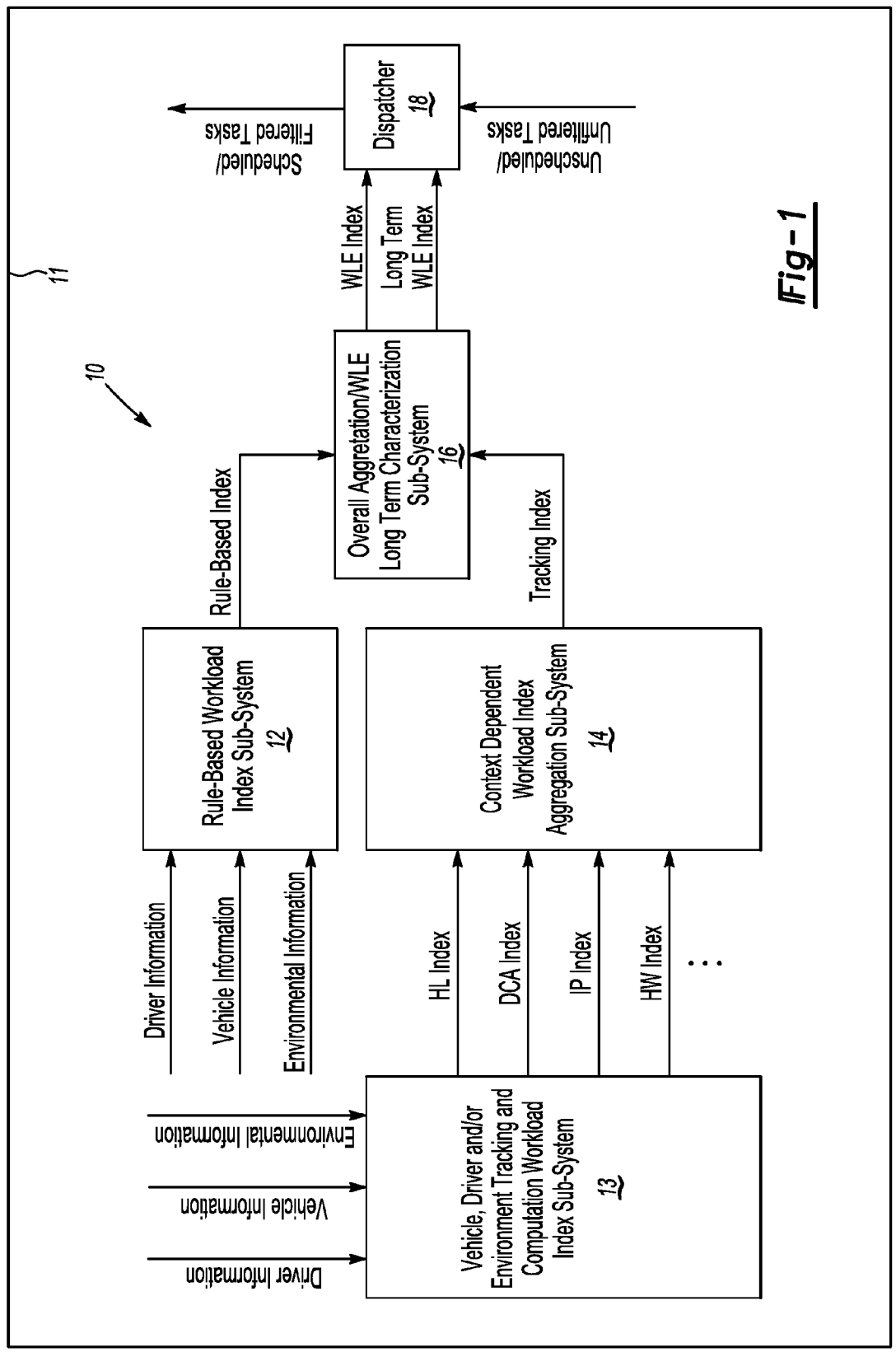
FIG. 1 is a block diagram of an example hybrid workload estimation system.

Driver workload/demand may refer to the visual, physical and cognitive demand that secondary activities such as infotainment, phone, proactive recommendations, etc. place on the driver above and beyond the primary activity of driving.

Drivers may sometimes incorrectly assume that they are able to divide their attention between the primary activity of driving and the secondary activities discussed above. Estimating the driving demand, therefore, may be of particular value if used to modulate communication and vehicle system interactions with the driver. Complex driving contexts, however, may require innovative prognostic approaches to driver workload estimation. Development of intelligent systems that enable the identification of driver workload may be useful in tailoring human machine interface (HMI) outputs to the driver.

For continuous workload estimation, it may be useful to design an estimator that predicts the workload under different driving contexts and/or drivers. Adaptation of vehicle cabin communication services may be based on the context within which the driving demand is predicted and the value of the services to the driver. In addition, characterizing the driver workload over periods of time (e.g., long term characterization) may be beneficial. Such assessment of the driver workload may allow vehicle cabin communication technologies to not only be suppressed or delayed during high workload periods, but in addition tailored to the long driving demand.

Certain embodiments described herein may provide methods and systems for Workload Estimation (WLE). The WLE may perform state estimation/classification of the driver workload from observable vehicle, driver and environment data for adaptive real-time HMI task management. The WLE, in certain situations, may use separate real-time techniques and/or employ a real-time hybrid approach to workload estimation. A rule-based algorithm, for example, may be supplemented with additional continuous prediction of driver workload based on the driver, vehicle and environment interactions. The WLE algorithms may incorporate specialized learning and computational intelligence techniques to compute and predict an aggregated WLE Index (e.g., a continuous signal representing a workload load estimate for the driver). The driver's driving demand may be inferred, in certain instances, from observable vehicle information including variations in speed, acceleration, braking, steering, headway, instrument panel and/or center stack interaction, etc.

The WLE Index may be used, for example, to set/avoid/limit/tailor voice commands and/or other tasks/information presented to the driver to improve functionality. Certain information for the driver may be limited/tailored/blocked during demanding vehicle handling manoeuvres, in hazardous driving environments, during periods of high activity with the instrument panel, etc.

Intelligent hybrid algorithmic approaches may account for long-term as well as short-term driver actions. WLE hybrid methods may capture the driver events, situations and behaviour for coordinating vehicle to driver communications. These and other techniques described herein may assist in predicting driver increasing/decreasing cognitive conditional states and use existing vehicle sensors.

The WLE Index may also allow a hierarchy of communication to be presented to the driver based on the driving demand/workload. Message priority (e.g., low, high, etc.) may determine whether the message is delivered to the driver during a particular instant based on the predicted load. Specific HMI information may also be presented to the driver based on the driver's long-term driving demand. Alternatively, a Hybrid WLE framework may incorporate GPS and digital map databases to account for road scenario situations and conditions. Information about the driver's physiological state including galvanic skin response, heart-rate, eye-gaze, head pose (i.e., position and orientation) and respiration may, in addition, be incorporated as inputs to the WLE framework for anomaly detection. In other examples, the predicted WLE index may be communicated to the driver to remind them to avoid secondary tasks under high workload conditions. Other scenarios are also possible.

FIG. 1 is a block diagram of an embodiment of a WLE system 10 for a vehicle 11. The system 10 may include a rule-based workload index sub-system 12, a vehicle, driver and environment tracking and computation workload index sub-system 13, a context dependent workload index aggregation sub-system 14, and an overall aggregation/WLE long term characterization sub-system 16. The sub-systems 12, 13, 14, 16 (individually or in combination) may be implemented as one or more controllers/processing devices/etc.

The sub-system 12 (as explained in section VII below) may take as input vehicle information, driver information and/or environmental information (available, for example, from the vehicle's controller area network (CAN)), and output a rule-based index representing driver workload. The sub-system 13 (as explained in sections III through VI below) may take as input vehicle information, driver information, and/or environmental information (available, for example, from the vehicle's CAN), and output one or more continuous indices (e.g., Handling Limit (HL) Index, Driver Control Action (DCA) Index, Instrument Panel (IP) Index, Headway (HW) Index) representing driver workload. The sub-system 14 (as explained in section VIII below) may take as input the index/indices generated by the sub-system 13, and output a Tracking (T) Index. The sub-system 16 (as explained in section VIII below) may take as input the rule-based index and T index, and output a WLE Index and/or (as explained in section IX below) a long term characterization of the WLE Index.

The system 10, in other embodiments, may lack the sub-systems 12, 14, 16. That is, certain embodiments may be configured to only generate one or more workload indices. As an example, the system 10 may be configured to only generate the IP Index based on certain vehicle information (discussed below). No aggregation is necessary in these circumstances as there is only a single measure of driver workload. Hence the WLE Index, in this example, is the IP index. The dispatcher 18, in these and other embodiments, may be configured to generate the long term characterization of the WLE Index. Other arrangements are also possible.

The WLE Index may be sent to a dispatcher 18, which may be implemented as one or more controllers/processing devices/etc. The dispatcher 18 (as explained in section X below) may act as a filter—preventing/delaying information to be communicated to the driver from reaching the driver based on the WLE Index. For example, if the WLE Index is greater than 0.8, all information intended for the driver may be blocked. If the WLE Index is approximately 0.5, only entertainment-type information may be blocked, etc. The dispatcher 18 may also schedule delivery of information to be communicated to the driver based on the WLE Index. For example, vehicle maintenance information, text-to-speech readouts, incoming calls, etc. may be delayed during periods of high workload. In addition, the dispatcher 18 may enable vehicle outputs to be tailored to the driver based on a long term WLE Index characterization as discussed in more detail below. For example, the output of certain vehicle systems including cruise control, adaptive cruise control, music suggestion, configurable HMI, etc. may be based on the long term driving demand.

The driver's workload state may be inferred from observable vehicle information including variations in speed, acceleration, braking, steering, headway, instrument panel interaction, etc. Table 1 lists example features/metrics related to driver workload load.

TABLE 1

Example Features/Metrics Related to Driver Workload

| Metric | Behavioral Effect Intended to Quantify |
|---|---|
| Mean Speed | Large speed increase/reduction |
| Maximum Speed | Large speed increase |
| Mean Time Headway (Gap Time) | Reduced headway |
| Minimum Time Headway | Reduced minimum headway |
| Brake Reaction Time (BRT) | Reduced BRT |
| Brake Jerks | Increased frequency |
| Steering Wheel Reversal Rate | Increased frequency of small reversals |
| Interaction with IP (e.g., pressing of IP buttons) | Increased frequency |
| Traffic Density | Increased density |
| Driving Location | New driving environment |
| Mean Speed | Large speed increase/reduction |
| Maximum Speed | Large speed increase |

Tables 2a and 2b list example information which may be available/accessible via CAN as known in the art. The following information may be used as inputs to any of the algorithms described herein.

TABLE 2a

Example Information Available via CAN

| | |
|---|---|
| Accelerator pedal position | Microphone inputs |
| Steering wheel angle | Cup holder sensor |
| Seat sensor | Vehicle speed |
| Turn signal | Yaw rate |
| Defrost signal | Lateral acceleration |
| Temperature control | Longitudinal acceleration |
| Headlamp status | Wheel speeds |
| High beam status | Throttle position |
| Fog lamp status | Master cylinder pressure |
| Radio tuner command | Driver request torque |
| Wiper status | Bus axle torque |
| Gear position | Bus torque distribution |
| Rain sensor | Roll rate |
| Configurable HMI | Sideslip angle |
| Touch HMI | Relative roll angle |

TABLE 2b

Example System Information Accessible via CAN

Traction Control System
Anti-Lock Braking System
Electronic Stability Control
Adaptive Cruise Control TABLE 2b-continued Example System Information Accessible via CAN Collision Mitigation by Braking
Blind Spot Monitoring
Automatic Parking Aid II. A Brief Discussion of Vehicle Stability Controls A vehicle's handling determines the vehicle's ability to corner and maneuver. The vehicle needs to stick to the road with its four tire contact patches in order to maximize its handling capability. A tire which exceeds its limit of adhesion is either spinning, skidding or sliding. A condition where one or more tires exceed their limits of adhesion may be called a limit handling condition and the adhesion limit may be called a handling limit. Once a tire reaches its handling limit, the average driver is usually no longer in control. In the so-called understeer case, the car under performs a driver's steering input, its front tires pass their handling limit, and the vehicle continues going straight regardless of the driver's steering request. In the so-called oversteer case, the car over performs the driver's steering inputs, its rear tires pass their handling limit, and the vehicle continues spinning. For safety purposes, most vehicles are built to understeer at their handling limits.

In order to compensate vehicle control in case a driver is unable to control the vehicle at or beyond the handling limit, electronic stability control (ESC) systems are designed to redistribute tire forces to generate a moment that can effectively turn the vehicle consistent with the driver's steering request. Namely, to control the vehicle to avoid understeer and oversteer conditions.

Since its debut in 1995, ESC systems have been implemented in various platforms. Phasing in during model year 2010 and achieving full installation by model year 2012, Federal Motor Vehicle Safety Standard 126 requires ESC systems on any vehicle with a gross weight rating below 10,000 lb. ESC systems may be implemented as an extension of anti-lock braking systems (ABS) and all-speed traction control systems (TCS). They may provide the yaw and lateral stability assist to the vehicle dynamics centered around the driver's intent. It may also proportion brake pressure (above or below the driver applied pressure) to individual wheel(s) so as to generate an active moment to counteract the unexpected yaw and lateral sliding motions of the vehicle. This leads to enhanced steering control at the handling limits for any traction surface during braking, accelerating or coasting. More specifically, current ESC systems compare the driver's intended path to the actual vehicle response which is inferred from onboard sensors. If the vehicle's response is different from the intended path (either understeering or oversteering), the ESC controller applies braking at selected wheel(s) and reduces engine torque if required to keep the vehicle on the intended path and to minimize loss of control of the vehicle.

A limit handling condition can be detected using data already existing in ESC systems, so new sensors may not be required. Consider, for example, a vehicle equipped with an ESC system using a yaw rate sensor, a steering wheel sensor, a lateral accelerometer, a wheel speed sensors, a master cylinder brake pressure sensor, a longitudinal accelerometer, etc. The vehicle motion variables are defined in the coordinate systems as defined in ISO-8855, where a frame fixed on the vehicle body has its vertical axis up, its axis along the longitudinal direction of the vehicle body, and its lateral axis pointed from the passenger side to the driver side.

Generally speaking, vehicle level feedback controls can be computed from individual motion variables such as yaw rate, sideslip angle, or their combination together with arbitrations among other control commands such as driver braking, engine torque request, ABS and TCS. Vehicle level control commands are discussed in the following.

The well-known bicycle model captures the vehicle dynamics, its yaw rate $\omega_z$ along the vertical axis of the vehicle body and its sideslip angle $\beta_r$ defined at its rear axle, and obeys the following equations:

$$I_z\dot{\omega}_z = -b_f c_f(\beta_r + b\omega_z v_x^{-1} - \delta) + b_r c_r \beta_r + M_z$$

$$M(\dot{v}_x\beta_r + v_x\dot{\beta}_r + b_r\dot{\omega}_z + \omega_z v_x) = -c_f(\beta_r + b\omega_z v_x^{-1} - \delta) - c_r\beta_r \quad (1)$$

where $v_x$ is the vehicle's travel speed, M and $I_z$ are the total mass and the yaw moment of inertia of the vehicle, $c_f$ and $C_r$ are the cornering stiffness of the front and rear tires, $b_f$ and $b_r$ are the distances from the center of gravity of the vehicle to the front and rear axles, $b=b_f+b_r$, $M_z$ is the active moment applied to the vehicle, and $\delta$ is the front wheel steering angle.

A target yaw rate $\omega_{zt}$ and a target sideslip angle $\beta_{rt}$ used to reflect the driver's steering intent can be calculated from (1) using the measured steering wheel angle $\delta$ and the estimated travel velocity $v_x$ as the inputs. In such a computation, we assume that the vehicle is driven on a road of normal surface condition (e.g., high friction level with nominal cornering stiffness $c_f$ and $C_r$). Signal conditioning, filtering and nonlinear corrections for steady state limit cornering may also be performed in order to fine tune the target yaw rate and the target sideslip angle. These calculated target values characterize the driver's intended path on a normal road surface.

The yaw rate feedback controller is essentially a feedback controller computed from the yaw error (the difference between the measured yaw rate and the target yaw rate). If the vehicle is turning left and $\omega_z \geq \omega_{rt} + \omega_{zdbos}$ (where $\omega_{zdbos}$ is a time varying deadband), or the vehicle is turning right and $\omega_z \leq \omega_{rt} - \omega_{zdbos}$, the vehicle is oversteering and activating the oversteer control function in ESC. For instance, the active torque request (applied to the vehicle for reducing the oversteer tendency) might be computed as in the following during a left turn: $M_z = \min(0, -k_{os}(\omega_z - \omega_{zt} - \omega_{zdbos}))$ during a right turn: $M_z = \max(0, -k_{os}(\omega_z - \omega_{zt} + \omega_{zdbos}))$ (2)

where $k_{os}$ is a speed dependent gain which might be defined as in the following $$k_{os} = k_0 + (v_x - v_{xdbl})\frac{k_{dbu} - k_{dbl}}{v_{xdbu} - v_{xdbl}} \quad (3)$$

with parameters $k_0, k_{dbl}, k_{dbu}, v_{xdbl}, v_{xdbu}$ being tunable.

If $\omega_z \leq \omega_z - \omega_{zdbus}$ (where $\omega_{zdbus}$ is a time varying deadband) when the vehicle is turning left or $\omega_z \geq \omega_z + \omega_{zdbus}$ when the vehicle is turning right, the understeer control function in ESC is activated. The active torque request can be computed as in the following during a left turn: $M_z = \max(0, -k_{us}(\omega_z - \omega_{zt} + \omega_{zdbus}))$ during a right turn: $M_z = \min(0, -k_{us}(\omega_z - \omega_{zt} - \omega_{zdbus}))$ (4)

where $k_{us}$ is a tunable parameter.

The sideslip angle controller is a supplementary feedback controller to the aforementioned oversteer yaw feedback controller. It compares the sideslip angle estimation $\beta_r$ to the target sideslip angle $\beta_{rt}$. If the difference exceeds a threshold $\beta_{rdb}$, the sideslip angle feedback control is activated. For instance, the active torque request is calculated as in the following
during a left turn, $$\beta_r \leq 0: M_z = \min(0, k_{ss}(\beta_r - B_{rt} - B_{rdb}) - k_{sscmp}\dot{\beta}_{rcmp})$$

during a right turn, $$\beta_r < 0: M_z = \max(0, k_{ss}(\beta - R_{rt} + B_{rdb}) - k_{sscmp}\dot{\beta}_{rcmp}) \quad (5)$$

where $k_{ss}$ and $k_{sscmp}$ are tunable parameters and $\dot{\beta}_{rcmp}$ is a compensated time derivative of the sideslip angle.

Other feedback control terms based on variables such as yaw acceleration and sideslip gradient can be similarly generated. When the dominant vehicle motion variable is either the yaw rate or the sideslip angle, the aforementioned active torque can be directly used to determine the necessary control wheel(s) and the amount of brake pressures to be sent to corresponding control wheel(s). If the vehicle dynamics are dominated by multiple motion variables, control arbitration and prioritization will be conducted. The final arbitrated active torque is then used to determine the final control wheel(s) and the corresponding brake pressure(s). For example, during an oversteer event, the front outside wheel is selected as the control wheel, while during an understeer event, the rear inside wheel is selected as the control wheel. During a large side-slipping case, the front outside wheel is always selected as the control wheel. When both the side slipping and oversteer yawing happen simultaneously, the amount of brake pressure may be computed by integrating both yaw error and the sideslip angle control commands.

Besides the above cases where the handling limit is exceeded due to the driver's steering manoeuvres, a vehicle can reach its limit handling condition in its longitudinal motion direction. For example, braking on a snowy and icy road can lead to locked wheels, which increases the stopping distance of the vehicle. Open throttling on a similar road can cause the drive wheels to spin without moving the vehicle forward. For this reason, the handling limit may also be used for these non-steering driving conditions. That is, the conditions where the tire longitudinal braking or driving forces reach their peak values may also be included in a definition of the handling limit.

The ABS function monitors the rotational motion of the individual wheels in relation to the vehicle's travel velocity, which can be characterized by the longitudinal slip ratios $\lambda_i$, with i=1, 2, 3, 4 for the front-left, front-right, rear-left and rear-right wheels, computed as in the following $$\lambda_1 = \frac{\kappa_1 \omega_1}{\max((v_x + \omega_z t_f)\cos(\delta) + (v_y + \omega_z b_f)\sin(\delta), v_{min})} - 1 \quad (6)$$

$$\lambda_2 = \frac{\kappa_2 \omega_2}{\max((v_x + \omega_z t_f)\cos(\delta) + (v_y + \omega_z b_f)\sin(\delta), v_{min})} - 1$$

$$\lambda_3 = \frac{\kappa_3 \omega_3}{\max(v_x - \omega_z t_r, v_{min})} - 1, \lambda_4 = \frac{\kappa_4 \omega_4}{\max(v_x + \omega_z t_r, v_{min})} - 1$$

where $t_f$ and $t_r$ are the half tracks for the front and rear axles, $\omega_i$ is the $i^{th}$ wheel speed sensor output, $\kappa_i$ is the $i^{th}$ wheel speed scaling factor, $v_y$ is the lateral velocity of the vehicle at its c.g. location, and $v_{min}$ is a preset parameter reflecting the allowable minimum longitudinal speed. Notice that (6) is only valid when the vehicle is not in the reverse driving mode. When the driver initiated braking generates too much slip (e.g., $-\lambda_i \geq \lambda_{bp} = 20\%$) at a wheel, the ABS module will release the brake pressure at that wheel. Similarly, during a large throttle application causing a large slip on the $i^{th}$ driven wheel, the TCS module will request engine torque reduction and/or brake pressure applied to the opposite wheel at the same axle. Consequently, ABS or TCS activations can be predicted by monitoring how close $\lambda_i$s are from $\lambda_{bp}$ and $\lambda_{tp}$.

III. Handling Limit Index

While the aforementioned ESC (including ABS and TCS) is effective in achieving its safety goal, further enhancement is still possible. For example, augmentation of ESC systems may be desirable for roll stability control. The appropriate correction which ESC tries to make, however, may be counteracted by the driver or ambient conditions. A speeding vehicle whose tire forces go far beyond the traction capability of the road/tires might not be able to avoid an understeer accident even with ESC intervention.

Generally speaking, accurate determination of the handling limit conditions would typically involve direct measurement of road and tire characteristics or intensive information from many related variables if direct measurements are not available. Currently, both of these methods are not mature enough for real-time implementation.

Due to their feedback feature, ESC systems may be configured to determine the potential limit handling conditions through monitoring the motion variables (vehicle handling parameters) of a vehicle such as those described in the last section. When the motion variables deviate from their reference values by a certain amount (e.g., beyond certain deadbands), the ESC systems may start to compute differential braking control command(s) and determine control wheel(s). The corresponding brake pressure(s) is then sent to the control wheel(s) to stabilize the vehicle. The starting point of the ESC activation can be thought of as the beginning of the handling limit.

More specifically, we may define a relative handling limit margin $h_x$ as in the following $$h_x = \begin{cases} \frac{\bar{x} - x}{\bar{x}} & \text{if } 0 \leq x \leq \bar{x} \\ \frac{x - \underline{x}}{\underline{x}} & \text{if } \underline{x} \leq x < 0 \\ 0 & \text{otherwise} \end{cases} \quad (7)$$

where x is the deviation of a motion variable from its reference value and $[\underline{x}, \bar{x}]$ defines the deadband interval within which x falls without initiating the ESC, ABS or TCS. x can be any of the control variables defined in the last section (or any other suitable control variable).

The benefit of $h_x$ defined in (7) is that the driving condition can be quantitatively characterized into different categories. For instance, when $h_x \leq 10\%$, the driving condition may be categorized as a red zone condition where the driver needs to have special attention or take some special actions (e.g., slowing down the vehicle); when $10\% < h_x \leq 40\%$, the driving condition may be categorized as a yellow zone condition which needs some level of special attention from the driver; when $40\% < h_x \leq 100\%$, the driving condition may be characterized as a normal condition. In the normal condition, the driver needs only to maintain his normal driving attention. Of course, other ranges may also be used.

More specifically, let us use the control variables computed in the last section to discuss the computation of $k_x$s. The vehicle's yaw handling limit margin during oversteer situations $h_{OS}$ (where $\omega_z > \omega_{zt}$ when the vehicle is turning to the left and $\omega_z > \omega_{rt}$ when the vehicle is turning to the right) can be computed from (7) by setting $x=\omega_z-\omega_{zt}$ and $\bar{x}=\omega_{zdbos}=-\underline{x}$, where $\omega_{zdbos}$ is the oversteer yaw rate deadband as defined in (2).

Similarly, the vehicle's yaw handling limit $h_{US}$ for understeer situations can be computed from (7) by setting $x=\omega_z-\omega_{rt}$ and $\bar{x}=\omega_{zdbus}=-\underline{x}$, where $\omega_{zdbus}$ is the understeer yaw rate deadband as defined in (4). Notice that the aforementioned deadbands might be functions of the vehicle speed, the magnitude of the target yaw rate, the magnitude of the measured yaw rate, etc. The deadbands for the understeer situation ($x<0$) and the oversteer situation ($x>0$) are different and they are tunable parameters.

The vehicle's sideslip handling limit margin $h_{SSRA}$ can be computed from (7) by setting $x=\beta_r-\beta_{rt}$ and $\bar{x}=\beta_{rdb}=-\underline{x}$.

The longitudinal handling limits of the vehicle involve the conditions when either the driving or braking force of the tires approaches the handling limit. The traction control handling limit margin for the $i^{th}$ driven wheel $h_{TCS_i}$ can be computed from (7) by setting $x=\lambda_i$, $\underline{x}=0$, and $\bar{x}=\lambda_{tb}$. The ABS handling limit margin for the $i^{th}$ wheel $h_{ABS_i}$ can also be computed from (7) by setting $x=\lambda_i$, $\underline{x}=\lambda_{bp}$, and $\bar{x}=0$. The final traction and braking handling limit margins may be defined as $$h_{ABS} = \min_{i \in \{1,2,3,4\}} h_{ABS_i}, \quad h_{TCS} = \min_{i \in \{1,2,3,4\}} h_{TCS_i} \qquad (8)$$

Notice that further screening conditions may be used in computing the aforementioned handling limit margins. For instance, one of the following or the combination of some of the following conditions might be used to set the handling limit margin as 0: a magnitude of the target yaw rate is beyond a certain threshold; a magnitude of the measured yaw rate is greater than a certain threshold; a driver's steering input exceeds a certain threshold; or, extreme conditions such as the vehicle's cornering acceleration is greater than 0.5 g, the vehicle's deceleration is greater than 0.7 g, the vehicle is driven at a speed beyond a threshold (e.g., 100 mph), etc.

In order to test the aforementioned handling limit margin computations and verify their effectiveness with respect to known driving conditions, a vehicle equipped with a research ESC system developed at Ford Motor Company was used to conduct vehicle testing.

Figure 2:
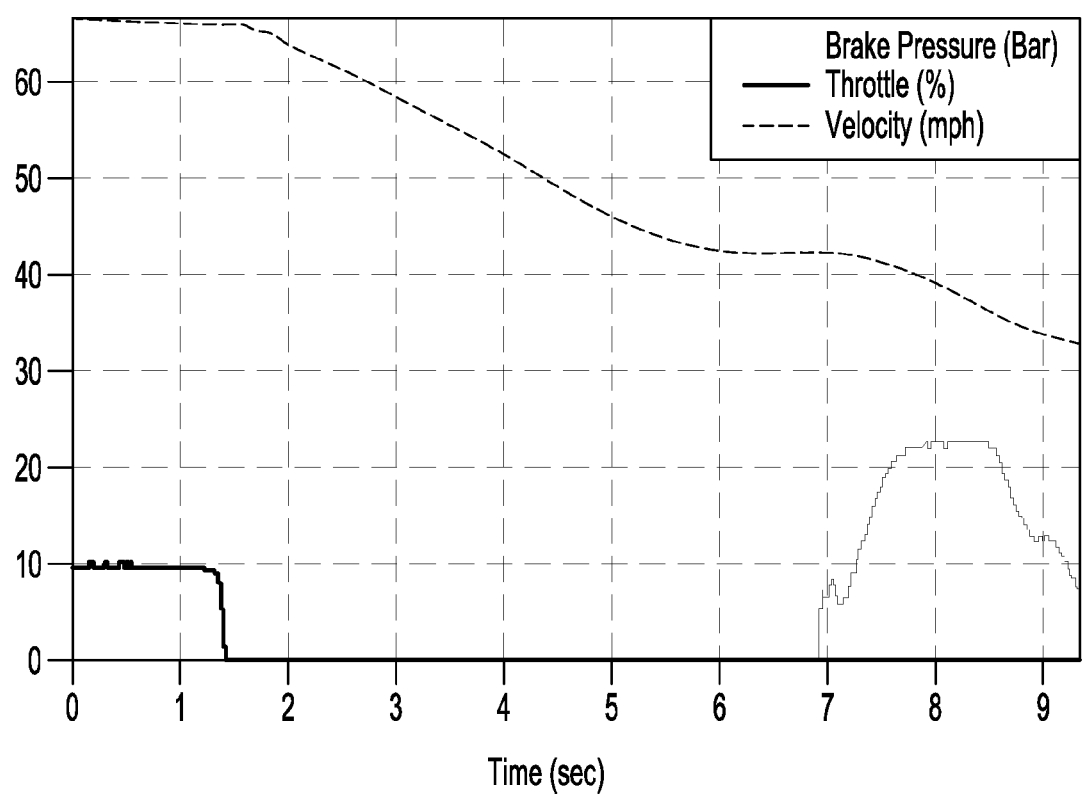
FIG. 2 is a plot of example vehicle speed, traction and braking profiles.
Figure 3A:
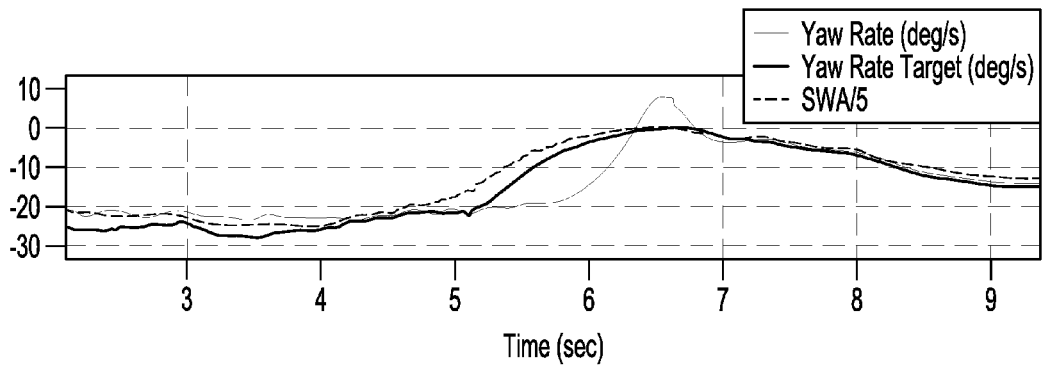
FIGS. 3A through 3C are plots of example vehicle motion states of yaw rate and sideslip angle.
Figure 3B:
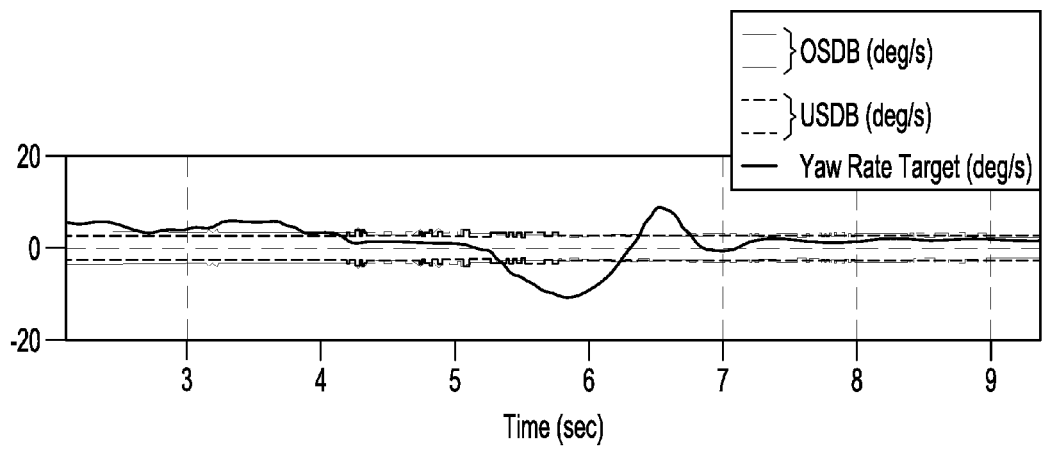
Figure 3C:
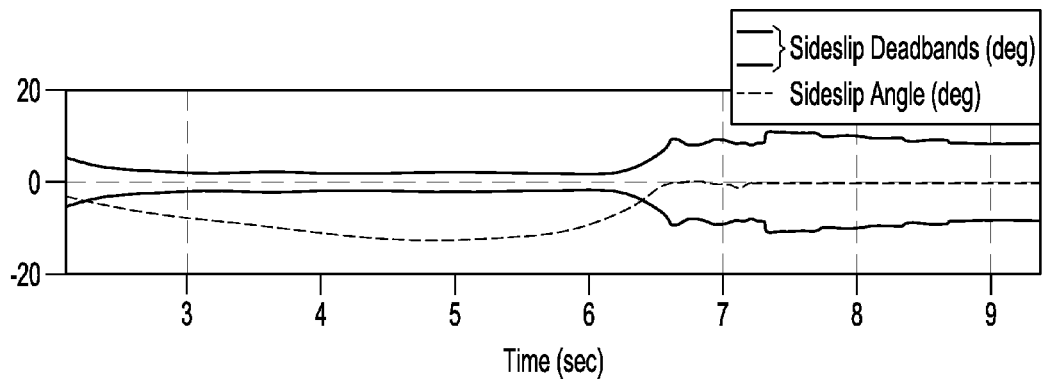
Figure 4A:
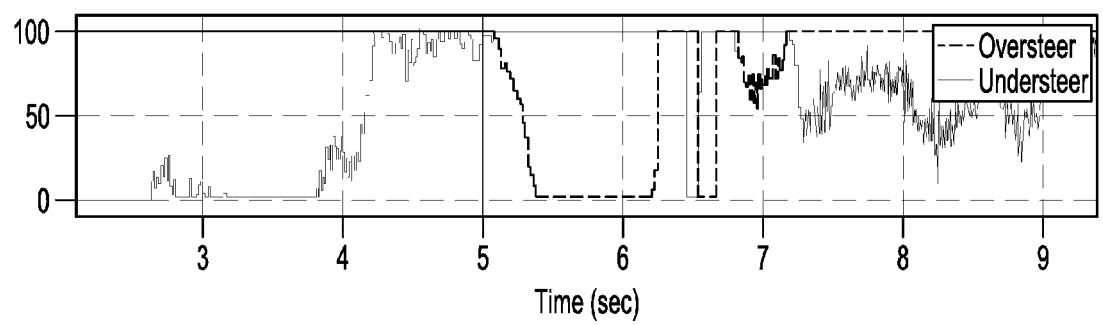
FIGS. 4A through 4C are plots of example yawing, longitudinal, and side slipping handling limit margins.
Figure 4B:
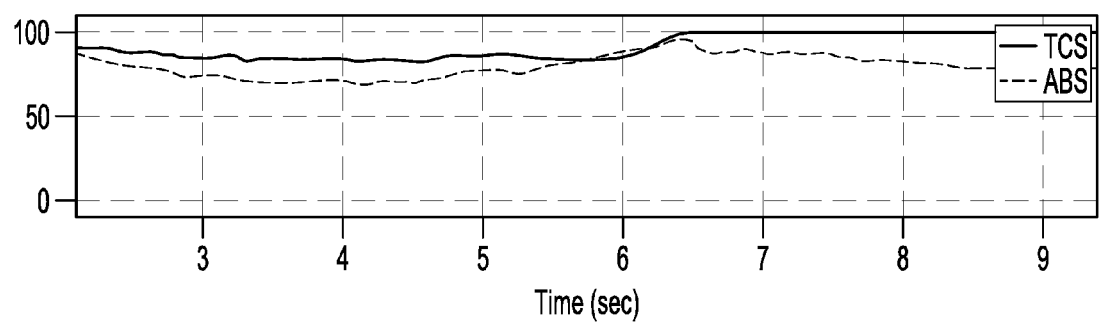
Figure 4C:
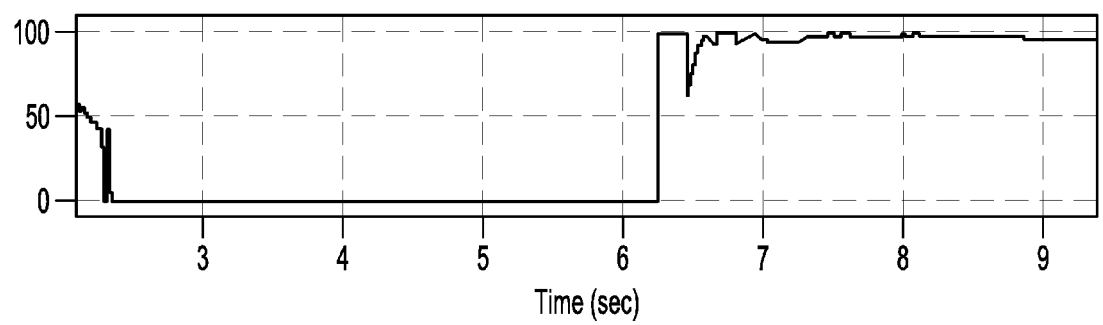

For the driving condition profiled by the vehicle speed, throttling, and braking depicted in FIG. 2, the measured and computed vehicle motion variables are shown in FIGS. 3A through 3C. The corresponding individual handling limit margins $h_{US}$, $h_{OS}$, $h_{TCS}$, $h_{ABS}$, and $h_{SSRA}$ are shown in FIGS. 4A through 4c. This test was conducted as a free form slalom on a snow pad with all ESC computations running. The brake pressure apply was turned off in order for the vehicle to approach the true limit handling condition.

Figure 5:
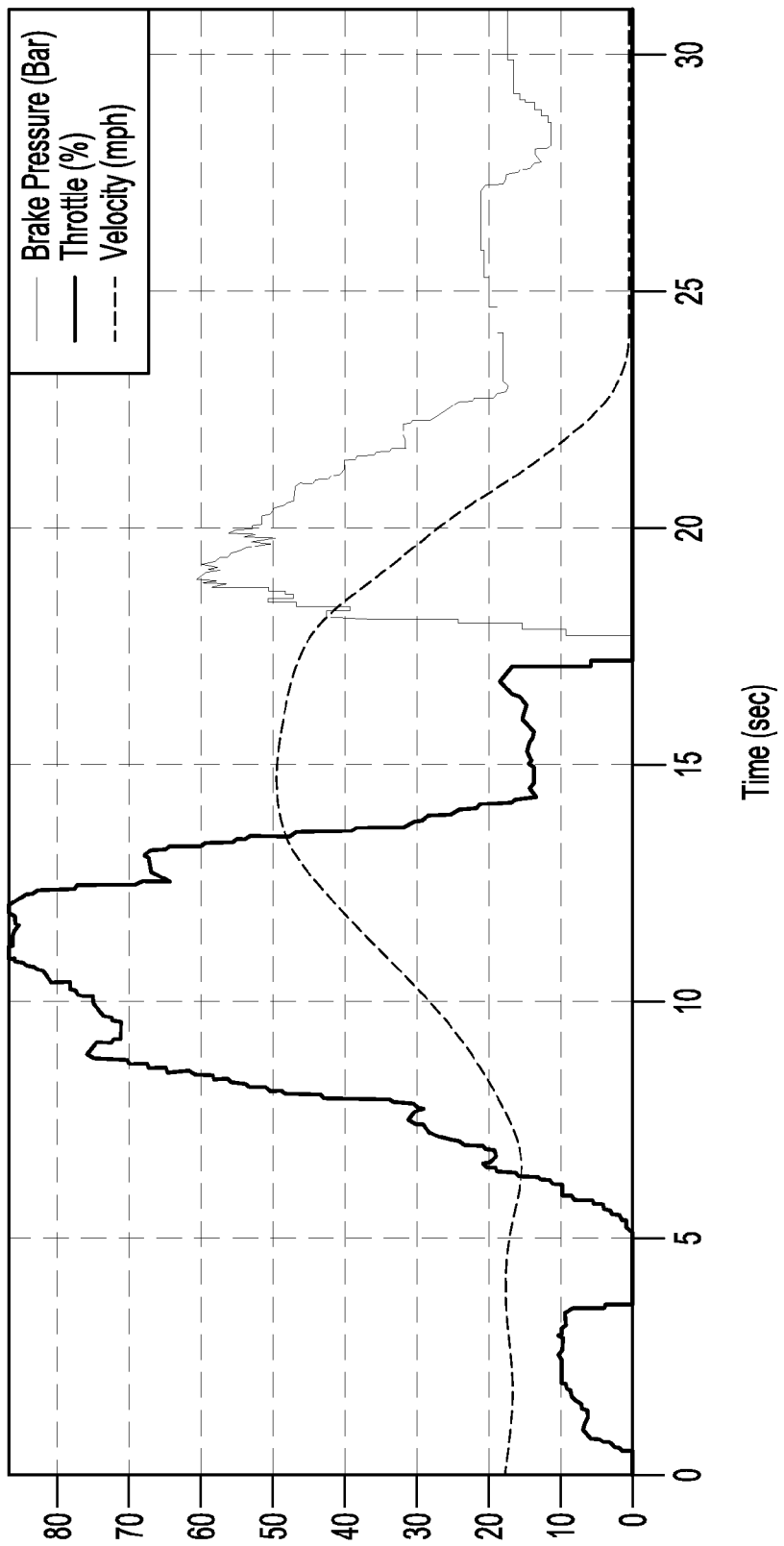
FIG. 5 is a plot of example vehicle speed, traction and braking profiles.
Figure 6A:
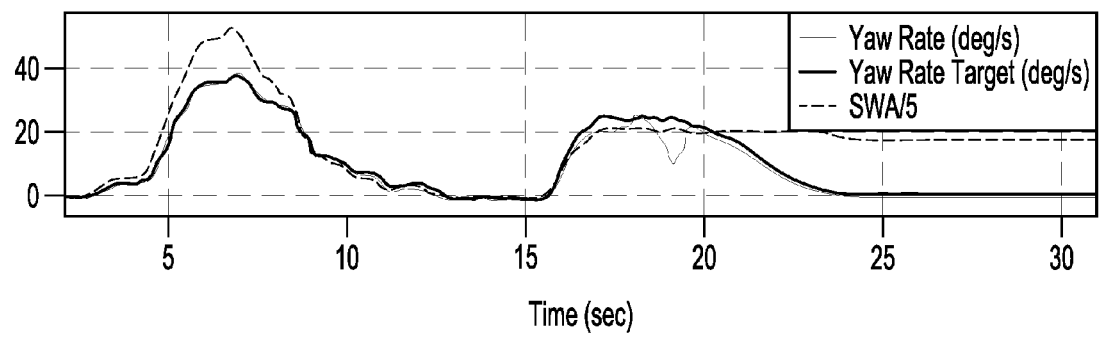
FIGS. 6A through 6C are plots of example vehicle motion states of yaw rate and sideslip angle.
Figure 6B:
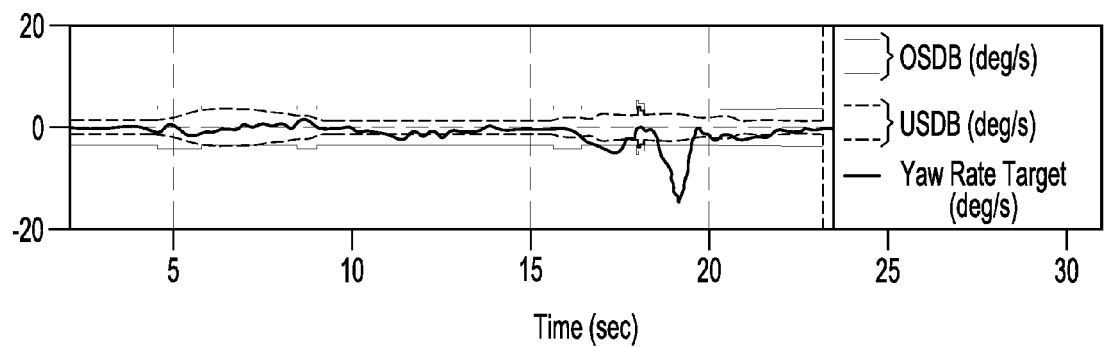
Figure 6C:
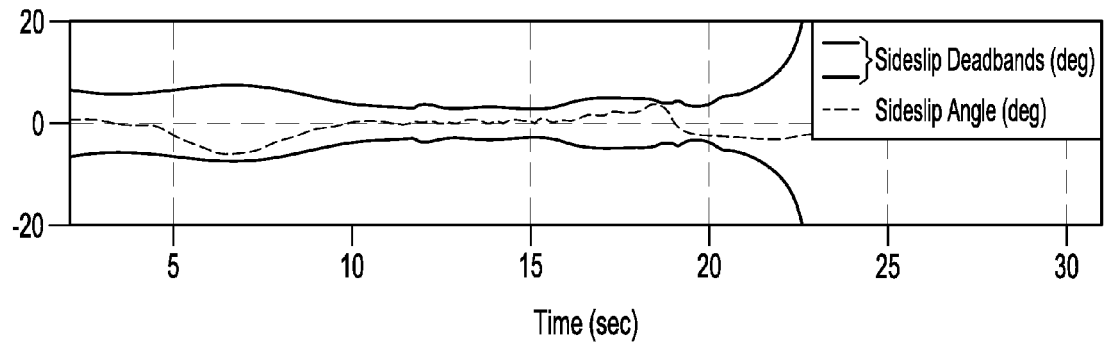
Figure 7A:
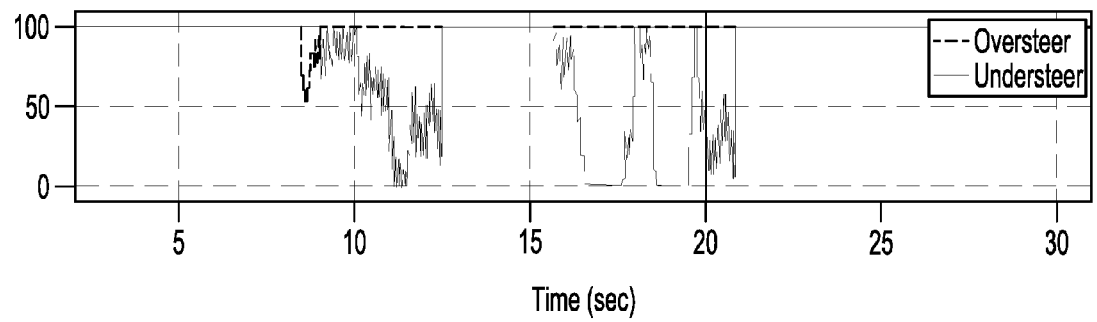
FIGS. 7A through 7C are plots of example yawing, longitudinal, and side slipping handling limit margins.
Figure 7B:
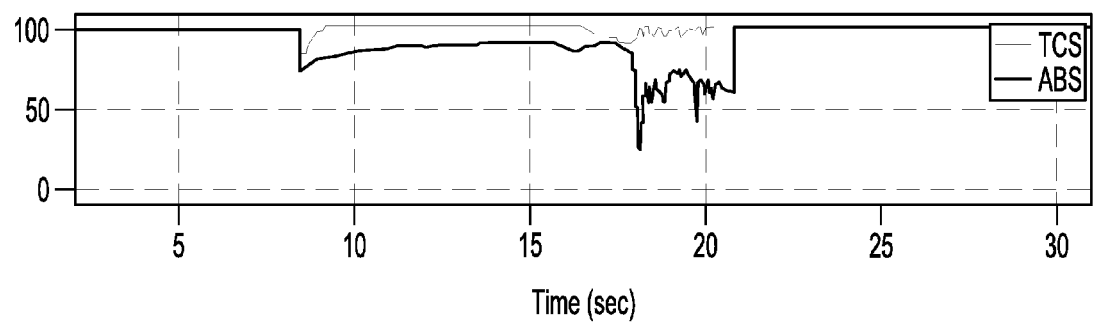
Figure 7C:
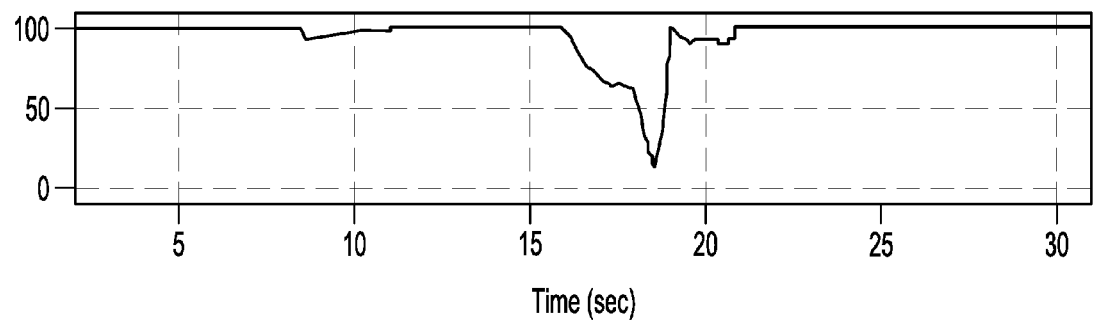

For another test, the vehicle was driven on a road surface with high friction level. The vehicle speed, traction and braking profiles for this test are depicted in FIG. 5. The vehicle motion states are shown in FIGS. 6A through 6C. The corresponding individual handling limit margins $h_{US}$, $h_{OS}$, $h_{TCS}$, $h_{ABS}$, and $h_{SSRA}$ are shown in FIGS. 7A and 7B.

An envelope variable of all the individual handling limit margins is defined as $$h_{env} = \min\{h_{OS}, h_{US}, h_{TCS}, h_{ABS}, h_{SSRA}\} \qquad (9)$$

Considering that sudden changes in the envelope handling limit margin might be due to signal noises, a low-pass filter $F(z)$ is used to smooth $h_{env}$ so as to obtain the final Handling Limit (HL) Index or margin $$h = F(z) h_{env} \qquad (10)$$

Figure 8:
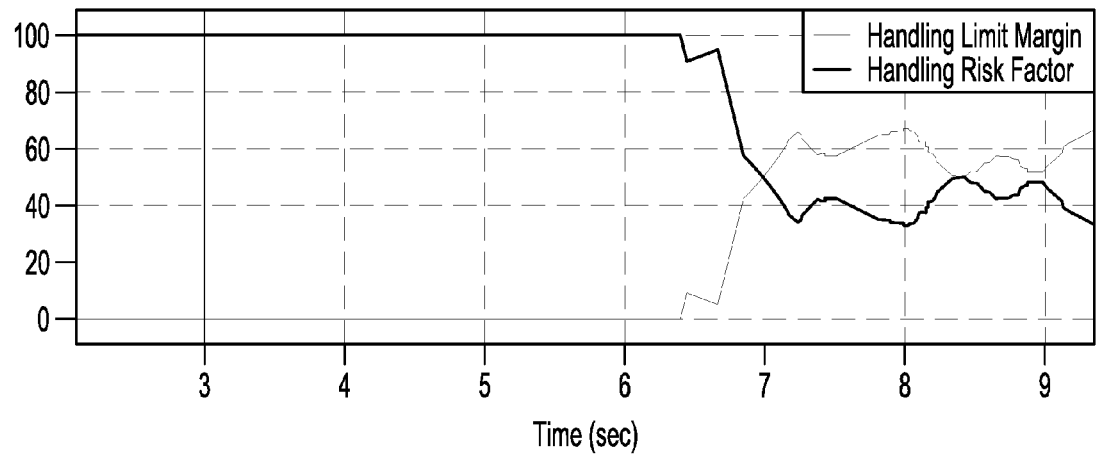
FIGS. 8 and 9 are plots of example final handling limit margins and risk.
Figure 9:
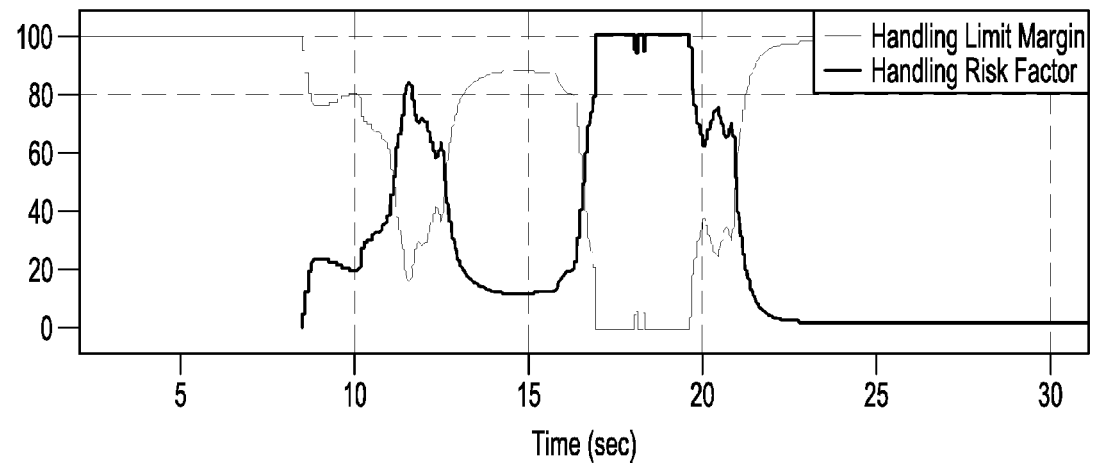

For the vehicle test data shown in FIG. 2 and FIGS. 3A through 3C, the final handling limit margin is depicted in FIG. 8, while for the vehicle test data shown in FIG. 5 and FIGS. 6A through 6C, the final handling limit margin is depicted in FIG. 9.

The HL Index may provide a continuous variable between 0 and 1 and indicate how close the driver is to the vehicle's handling limit (where a value of 1 indicates that the driver is at the vehicle's handling limit). This model-based HL Index may provide particularly important driving demand information during, for example, low-μ road driving conditions.

Assuming that more visual, physical and cognitive attention is required to maintain vehicle control as the vehicle approaches its handling limit, driver workload information may be inferred from the HL Index. As the workload on the driver increases, the HL Index increases. As the workload on the driver decreases, the HL Index decreases.

IV. Driver Control Action Index

The Driver Control Action (DCA) Index may provide a continuous variable between 0 and 1 that indicates the total variability of the driver's control action (or activity level) with respect to, for example, acceleration, braking, steering, heart-rate, respiration, eye-gaze, head pose, galvanic skin response, etc. Such driver-related data can be collected, for example, using any suitable or known sensors (e.g., hear-rate sensors, cameras, etc.) Increased variability from the driver's operational norm may reflect increased driving demand and vise-versa. The DCA Index may thus provide a measure of the variability (driving demand) associated with different drivers having different norms of vehicle control action (or activity level).

Figure 10:
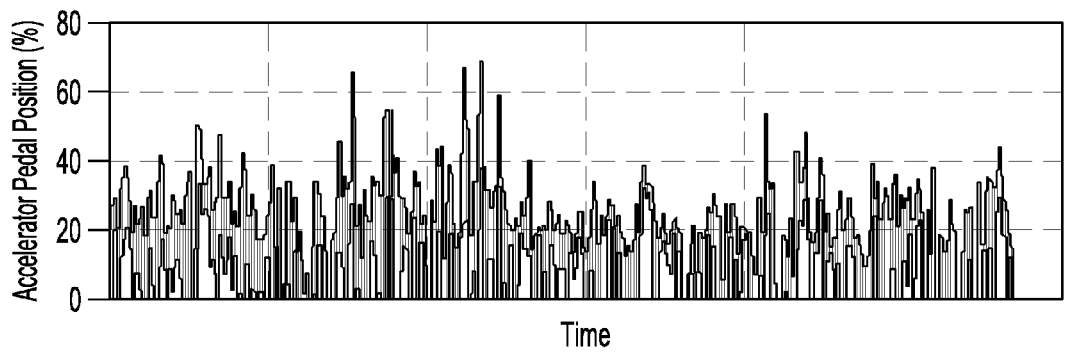
FIGS. 10 and 11 are plots of example accelerator pedal position for high demand circumstances and low demand circumstances respectively.
Figure 11:
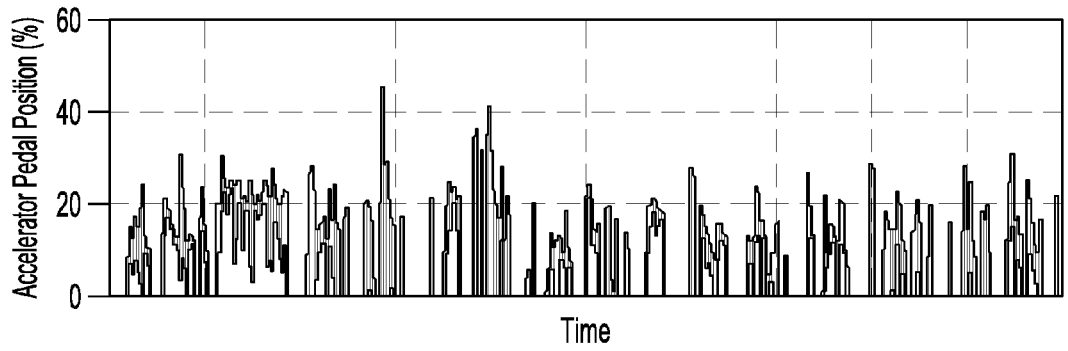

Consider, for example, the impact of the accelerator pedal variability on driving demand. Referring to FIGS. 10 and 11, real-time accelerator pedal positions are plotted versus time for example high demand and low demand circumstances, respectively. Considerably more variability of the accelerator pedal is evident in the high demand case relative to the low demand case. Driver physiological state (e.g., heart-rate, respiration, eye-gaze, head pose, galvanic skin response, etc.) also exhibits characteristic variability as demand changes.

Figure 12:
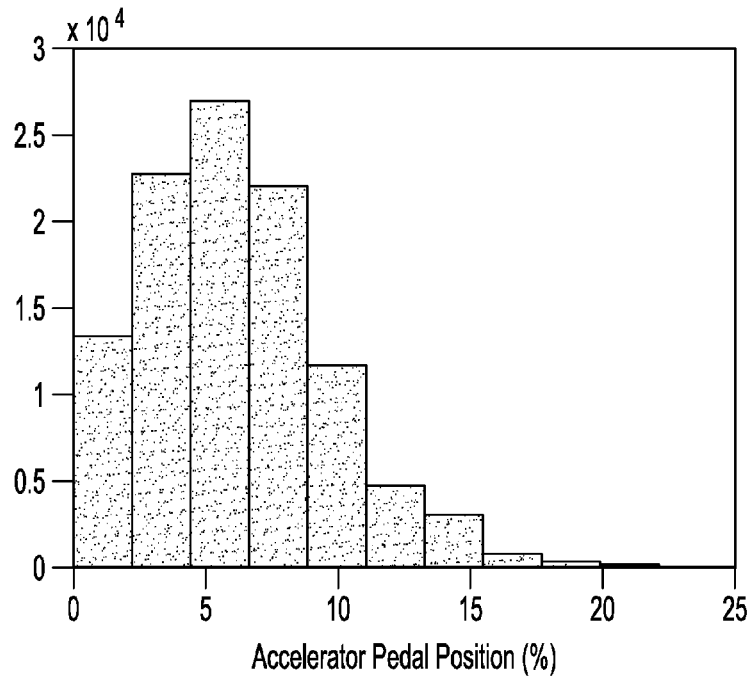
FIGS. 12 and 13 are histograms of the standard deviation of the accelerator pedal position of FIGS. 10 and 11 respectively.
Figure 13:
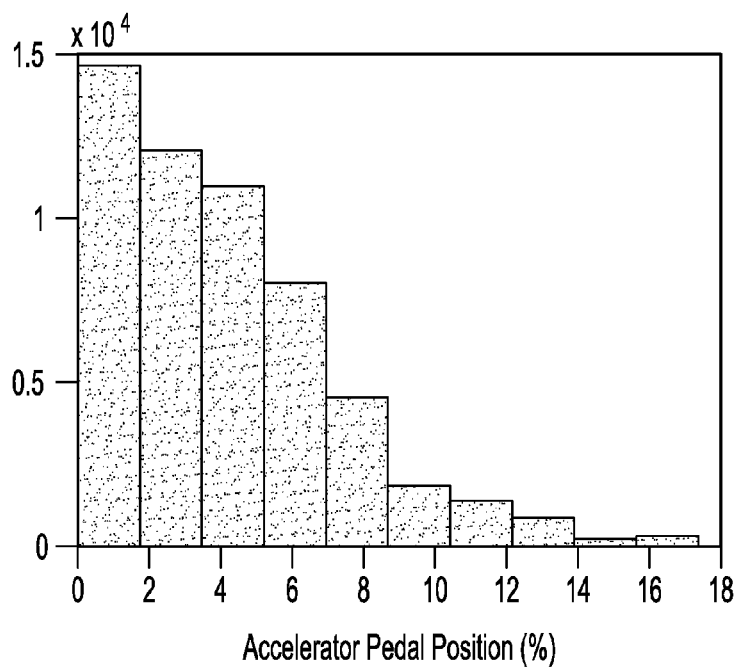

The standard deviation of the accelerator pedal positions of FIGS. 10 and 11 are plotted respectively in FIGS. 12 and 13.

Figure 14:
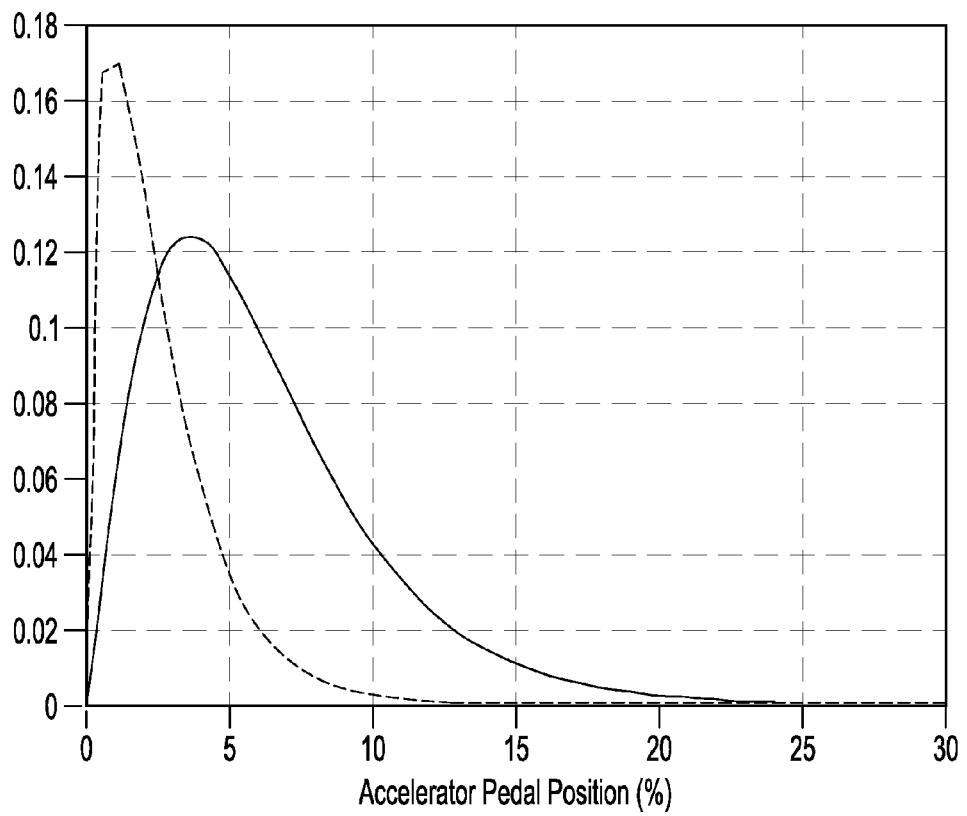
FIG. 14 is a plot of curves fit to the histograms of FIGS. 12 and 13.

Referring to FIG. 14, probabilistic fits to the distributions of FIGS. 12 and 13 are generated using a gamma function of the standard form $$y = f(x \mid a, b) = \frac{1}{b^a \Gamma(a)} x^{(a-1)} e^{\left(-\frac{x}{b}\right)} \qquad (11)$$

where a is the scale factor and b is the shape factor. The dashed line represents the low driving demand standard deviation distribution and the solid line represents the high driving demand standard deviation distribution. These probabilistic distributions of the accelerator pedal variability show levels of distinction between the driving demand categories and present opportunities for classification. For example, a standard deviation of 2% would have a higher probability of being characteristic of low driving demand, whereas a standard deviation of 10% would have a higher probability of being characteristic of high driving demand, etc. This technique may similarly be applied to brake pedal position, steering wheel angle, and/or other driver control action parameters. Hence, the DCA Index may estimate the driving demand based on the variability of the driver action on the accelerator pedal, brake pedal, steering wheel, etc.

The averages of the standard deviation variability shown in FIG. 14 can change with different drivers. The DCA Index computation may account for these changing averages and compute the relative variability. The derivative of the driver inputs may also be incorporated to capture anticipatory action. This variance computation may be obtained from analysis of the determinant of the covariance for each of the factors (e.g., accelerator pedal position/rate, brake pedal position/rate, steering wheel angle position/rate, heart-rate/rate of change of heart-rate, respiration/rate of change of respiration, etc.)

The DCA Index, in certain embodiments, is computed by recursively calculating the determinant of the covariance affecting driving demand for each of the factors based on the following equations:

$$\Delta x_k = x_k - \bar{x}_k \tag{12}$$

$$\bar{x}_{k+1} = (1-\alpha)\bar{x}_k + \alpha \cdot x_k \tag{13}$$

$$G_{k+1} = \left[\frac{(I - P_k \cdot \Delta x_k) \cdot G_k}{(1-\alpha)}\right] \tag{14}$$

$$P_{k+1} = G_k \cdot \Delta x_k^T \cdot \frac{\alpha}{(1-\alpha) + \alpha \cdot \Delta x_k \cdot P_k \Delta x_k^T} \tag{15}$$

where $x_k$ is a 2-dimensional vector for each of the driver control actions and its derivative (at time instant k), $\bar{x}_k$ is the mean (which may be continuously updated during each drive cycle, and reset after each drive cycle), $\alpha$ is a calibrated forgetting factor, $G_k$ is the estimated inverse covariance matrix, I is the identity matrix, $P_k$ is the estimated covariance matrix, and $\Delta x_k^T$ is the transpose of $\Delta x_k$ from (12).

The recursively computed determinant of the covariance matrix, det, is given by $$\det_{k+1} = (1-\alpha)^n \det_k \cdot (1+\alpha \cdot \Delta x_k \cdot G_k \cdot \Delta x_k^T) \tag{16}$$

where n is the size of the vector $x_k$. It provides a measure of the estimated variability of the driver acceleration, braking, steering, heart-rate, respiration, eye-gaze, head pose, galvanic skin response, etc. relative to a particular driver's mean for these parameters. It also provides a single dimensional measure of total variance which may be tracked to capture significant changes in aggregated variability of driver control actions (or activity level).

The final DCA Index may be scaled to a continuous signal between 0 and 1 and be given by $$DCA \text{ Index} = \max(\text{Accel Ped Variance}, \text{Brake Ped Variance}, \text{Steering Variance}, \text{etc.}) \tag{17}$$

Accelerator pedal position as plotted in FIG. 15A and steering wheel angle as plotted in FIG. 15B have been analyzed using the techniques above. FIG. 15C shows example output for the DCA Index based on the input of FIGS. 15A and 15B. The determinant of the covariance matrix (16) provides a measure, in this example, of the estimated variability of the driver acceleration and steering performance. The respective variabilities have been normalized and aggregated by taking their maximum values to yield the DCA Index as plotted in FIG. 15C. Vehicle speed is plotted in FIG. 15D for reference. Increased variability is captured on the DCA Index scale as values closer to 1 (indicative of higher driving demand), while decreased variability is captured on the scale as values between, for example, 0 and 0.2 (indicative of low driving demand).

A unit dimensional vector (signal) representing physiological response may be applied to minimize computational resources in other examples. The output measurements from driver heart-rate, respiration, eye-gaze, galvanic skin response, etc. may undergo recursive signal processing based on equation 13. The index is then obtained by directly computing the normalized variance recursively. This may provide a direct measure of driver condition based on activity and workload for tailored vehicle information and connectivity management. The index may be directly incorporated for vehicle and connected services information coordination, or may be aggregated in an overall workload estimator index.

V. Instrument Panel Index

Driver interaction with the instrument panel and/or other touch/voice related interfaces may provide an indication of driver activity. An increase in such driver activity level may increase the cognitive demands on the driver. As indicated in Table 1, an increase in driver button pressing activity may increase the driver workload. The frequency of interaction with cabin controls including the wiper control, climate control, volume control, turn indicator, center stack console, window control, power seat control, voice command interface, etc. may be aggregated into a composite index. The Instrument Panel (IP) Index thus provides a continuous output (between 0 and 1) representing the interaction of the driver with the instrument panel, electronics, and/or any other HMI.

When a button/interface device is pressed/engaged at any time instant k, for example, the output is given by, $$BP_i(k) = \alpha \cdot BP_i(k-1) + (1-\alpha) \cdot 1 \tag{18}$$

When a button/interface device is not pressed/engaged, the output is given by $$BP_i(k) = \alpha \cdot BP_i(k-1) + (1-\alpha) \cdot 0 \tag{19}$$

where $BP_i$ is the button/interface pressed/engaged tracking value for each button/interface being tracked, and $\alpha$ is a calibratable forgetting factor.

The IP Index output may then be given by $$IP \text{ Index} = \max(BP_1, BP_2, BP_{31}, BP_4 \ldots BP_n) \tag{20}$$

where n is the number of buttons/interfaces being tracked. The IP index may also be determined using any of the aggregation techniques described herein. As an example, techniques similar to those described with reference to (28) and (29) below may be used, etc.

Example turn indicator and air conditioning activity inputs are plotted respectively in FIGS. 16A and 16B. The resulting IP Index is determined according to (18), (19) and (20) and plotted in FIG. 16C. The rise time and steady state value, in this example, are based on the duration of the activity.

VI. Headway Index

The Headway Index provides a continuous variable between 0 and 1 and indicates how close the vehicle being driven is to the vehicle (or other object) in front of (or beside) it. As indicated in Table 1, increased workload load may be inferred from reduced mean time headway and/or reduced minimum headway.

Current velocity dependent headway may be obtained from $$HW_{curr} = \frac{(r_p(k) - r_f(k))}{v_f(k)} \quad (21)$$

where $r_p(k)$ is the position of the preceding vehicle at any time instant k, $r_f(k)$ is the position of the following vehicle and $v_f(k)$ is the velocity of the following vehicle. The mean headway, $HW_m(k)$, may be obtained from $$HW_M(k) = HW_M(k-1) + \alpha(HW_{curr} - HW_M(k-1)) \quad (22)$$

where $\alpha$ is a time constant for exponential filtering, which may be selected as desired. The HW Index may then obtained from $$HW\ \text{Index} = \left[ \gamma \left( 1 - \frac{HW_M}{HW_{MAX}} \right) \right] \quad (23)$$

where $\gamma$ is the HW Index sensitivity gain and $HW_{MAX}$ is a calibrated value. The gain may be chosen/adapted depending on the headway time required to meet a maximum index of 1.

The sensitivity gain, in other embodiments, may be chosen/adapted based on, for example, driver type. If a driver type such as "young," "old," "teen," "novice," "expert," etc. is known, the sensitivity gain may be adjusted accordingly. A driver may be identified as "young," "old," "teen," etc. based on a token carried by them as known in the art. The token may be detected by the vehicle and used to identify the type of driver. Alternatively, the vehicle may provide a select button that lets the driver identify themselves by type. Any suitable/known technique for classifying a driver by type, however, may be used. The sensitivity gain may be increased for "teen" and "novice" drivers, while the sensitivity gain may be decreased for "expert" drivers, etc. The sensitivity gain, in other embodiments, may be selected to be higher for "teen" and "novice" drivers and selected to be lower for "expert" drivers, etc. Hence the HW Index, given the same headway, may be higher for a "teen" driver and lower for an "expert" driver, etc.

Alternatively (or in addition to), the sensitivity gain may be chosen/adapted based on environmental conditions. Wet or icy road conditions, determined by any suitable/known technique such as through the detection of wheel slip, may result in the sensitivity gain being increased. Dry road conditions may result in the sensitivity gain being decreased. Any suitable environmental conditions including traffic density, geographic location, etc. may be used to select/alter the sensitivity gain.

Headway proximity to infrastructure including intersections, roadwork, high-demand roadway geometry, etc. may also be similarly computed as in (21), (22) and (23). In such cases, the HW Index output may be given by $$HW\ \text{Index} = \max(HW_1, HW_2, \ldots HW_n) \quad (24)$$

where n is the number of headway proximity items of high-driving demand being tracked. A weighted function for equation (24) may also be used.

Increased headway returns from increased traffic in adjacent lanes may be used as a bias input to the HW Index in other embodiments. (Increased traffic density may increase driving demand as indicated in Table 1.)

The time-to-collision, in still other embodiments, may be tracked in the regime of less than 1000 ms. In potential imminent crash conditions, the HW Index output may default to the max value of 1.

Figure 17:
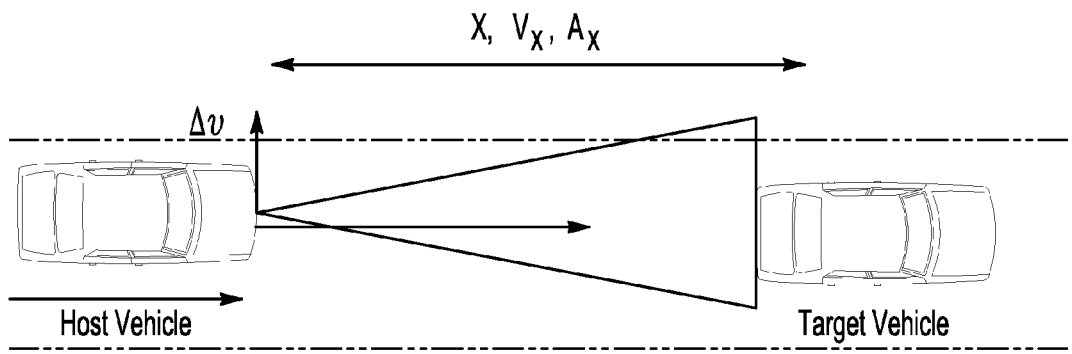
FIG. 17 is a schematic diagram of a vehicle following another.

Referring to FIG. 17, the time to collision, $t_c$, may be computed as follows $$t_c = \frac{-V_x \pm \sqrt{(V_x)^2 + 2(A_x)(X)}}{(A_x)} \text{ or } t_c = \frac{X}{V_x} \quad (25)$$

where $V_x$ is the closing velocity, $A_x$ is the relative acceleration, and X is the distance between the vehicles. The distance and closing velocity information may be obtained from any suitable/known radar system, vision system, lidar system, vehicle-to-vehicle communication system, etc.

Figure 18:
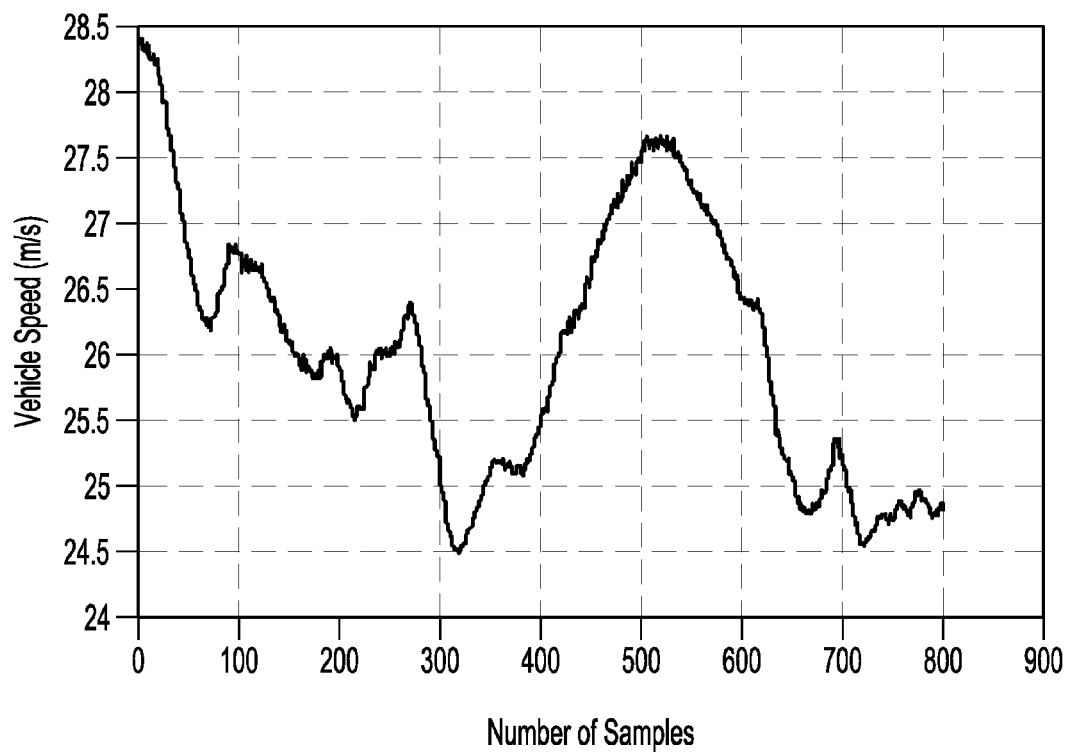
FIGS. 18, 19 and 20 are example plots of vehicle speed, closing velocity and range, respectively.
Figure 19:
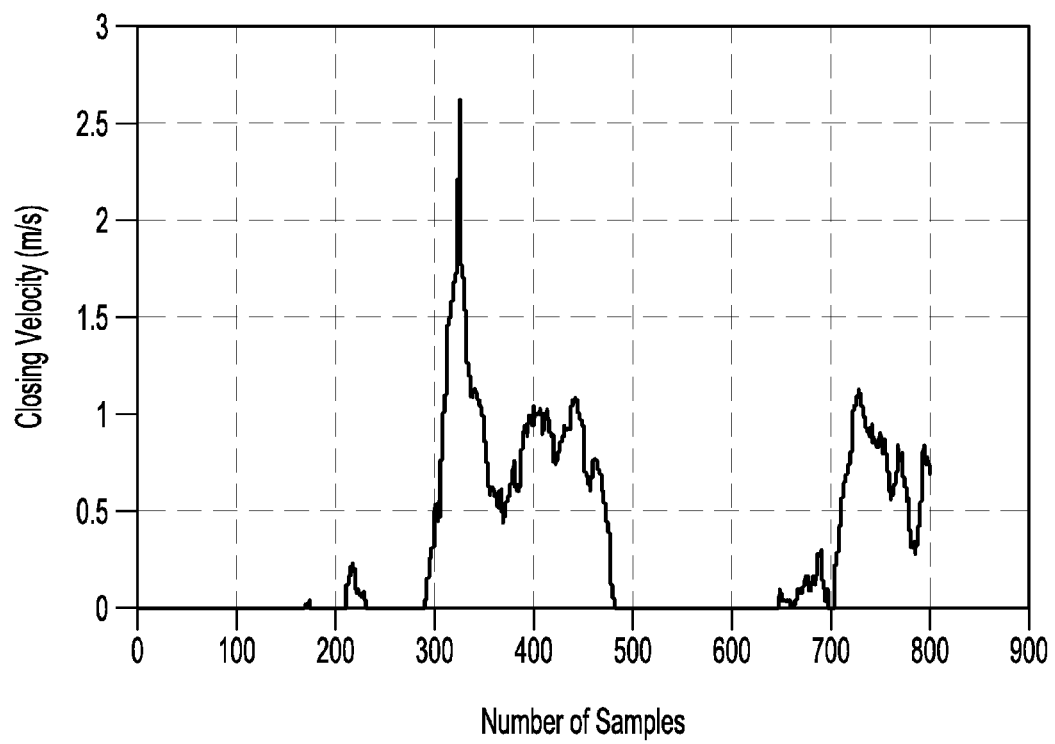
Figure 20:
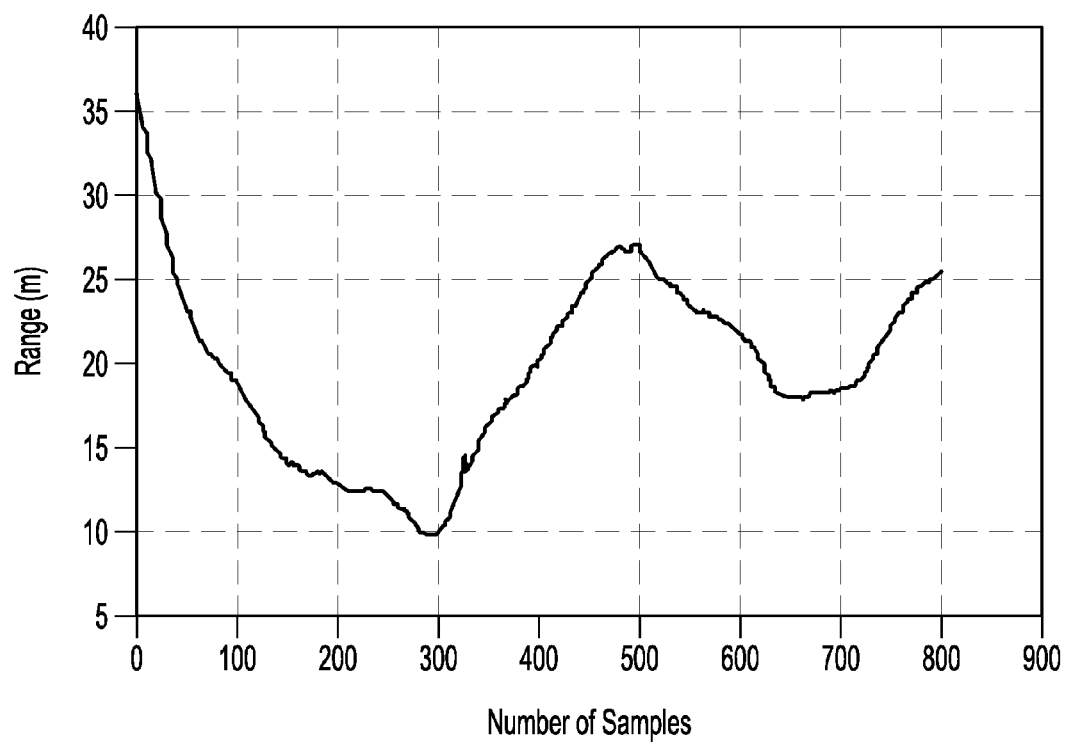
Figure 21:
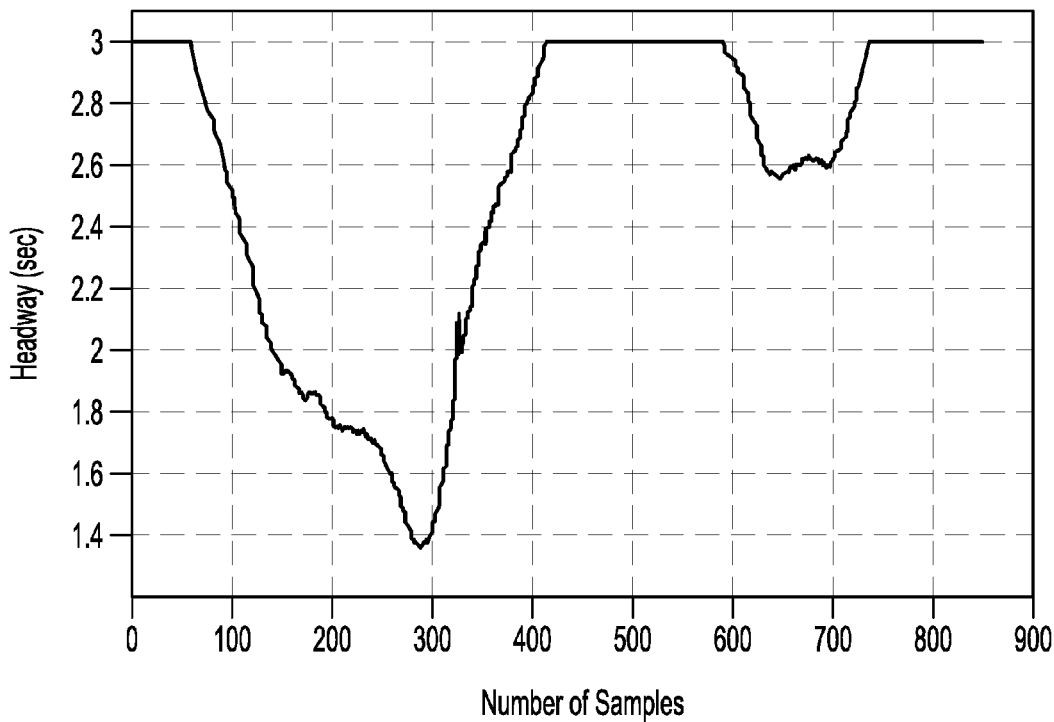
FIGS. 21 and 22 are example plots of headway and Headway (HW) Index respectively.
Figure 22:
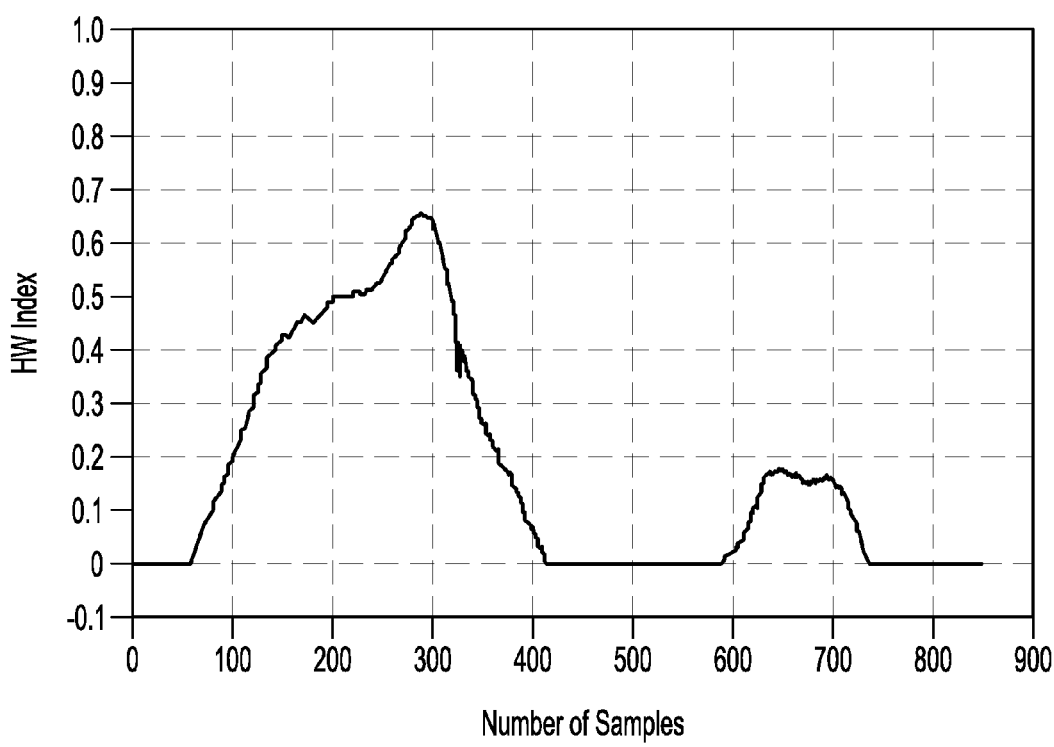

Considering the computation of the HW Index in an example vehicle following scenario, FIGS. 18 through 20 show the host vehicle speed, inter-vehicle closing velocity and range during the scenario. FIGS. 21 and 22 show the mean headway (as computed via (22)) and the HW Index (as computed via (23)), respectively.

VII. Rule-Based Sub-System

Referring again to FIG. 1, the rule-based sub-system 12 may include a knowledge base and facts for determining an event binary output flag. The sub-system 12 may provide specific expert engineering and vehicle-driver-environment interaction rules to supplement the other components of the system 10. The knowledge may be represented as a set of rules. Specific activation of vehicle systems may be incorporated.

Each rule specifies a recommendation of the output workload, and has the IF (condition), THEN (action) structure. When the condition part of a rule is satisfied, the action part is executed. Each rule may specify a recommendation of the output workload (0 or 1). A number of vehicle parameters including longitudinal acceleration, lateral acceleration, deceleration, steering wheel angle, button usage, etc. (see, e.g., Tables 2a and 2b) may be monitored/obtained in any suitable/known fashion by the sub-system 12 from, for example, the vehicle's CAN bus. Facts associated with these parameters and their combination may be used to set the conditional rules.

A general rule implemented by the sub-system 12 may be of the form, $$\text{If} \quad (26)$$

Vehicle_parameter $1 \rangle x_i$ and Vehicle_parameter $2 \rangle y_i$

Then $$\text{Event\_Flag} = \begin{cases} 1 & \text{if condition is satisfied} \\ 0 & \text{otherwise} \end{cases}$$

Specific delays or restriction of infotainment or vehicle cabin systems during events are enabled from the expert rules. The rule-based output may be further processed to provide a relative output aggregation based on the usage of a specific feature and the expert notion of the driving demand for the condition.

Rules may be based on the information, for example, listed in Tables 2a and 2b above. For example, if steering wheel angle>105 degrees, then Event_Flag=1. Other rules may also, of course, be constructed.

VIII. Aggregation

One or more of the HW Index, DCA Index, IP Index, and HL Index may be aggregated by the sub-system 14 to form a Tracking (T) Index using techniques described below. In embodiments where only one index is used/computed/determined however, no aggregation may be necessary.

In certain embodiments, short-term aggregation may be used to schedule/delay/suppress information/tasks to be communicated to the driver. For conditions where the highest driving demand assessed is required, the T Index may be given by $$T \text{ Index} = \max(DCA \text{ Index}, IP \text{ Index}, HL \text{ Index}, HW \text{ Index}) \quad (27)$$

In other embodiments, a context dependent aggregation is employed for mean/max output combinations of the index values as described below. With reference to FIG. 1 for example, the DCA Index, IP Index, HL Index, and HW Index may be combined by the sub-system 14 to form a T Index given by $$T \text{ Index} = \frac{\sum_{i=1}^{N} w_i y_i}{\sum_{i=1}^{N} w_i} \quad (28)$$

where $w_i$ are context dependent weights depending on the driving demand value placed on the input. Expansion of (28) yields $$T \text{ Index} = \frac{WLE_{DCA} w_{DCA} + WLE_{IP} w_{IP} + WLE_{HL} w_{HL} + WLE_{HW} w_{HW}}{w_{DCA} + w_{IP} + w_{HL} + w_{HW}} \quad (29)$$

Max(Tracking_Index) = 1.0 where $WLE_{DCA}$, $WLE_{IP}$, $WLE_{HL}$ and $WLE_{HW}$ are the DCA Index, IP Index, HL Index, and HW Index outputs respectively. The corresponding weights are given by $w_{DCA}$, $w_{IP}$, $w_{HL}$ and $w_{HW}$.

Tables 3 and 4 list example rules for aggregation.

TABLE 3

Example Rules for Context Based Aggregation

| Rule | If DCA Index is | If IP Index is | If HL Index is | If HW Index is | Then Calculate WLE Index; Max = 1.0 Min = 0.0; If night, then bias = +0.2 |
|---|---|---|---|---|---|
| 1 | Hi | Hi | Hi | Hi | Mean of 4 Indices: w(vector) = [1 1 1 1] |
| 2 | Hi | Hi | Hi | Low | Mean of 3 of Indices: w(vector) = [1 1 1 0] |
| 3 | Hi | Hi | Low | Low | Mean of 2 Indices: w(vector) = [1 1 0 0] |
| 4 | Hi | Low | Low | Low | Max: w(vector) = [0 1 0 0] |
| 5 | Low | Hi | Low | Low | Max: w(vector) = [0 1 0 0] |
| 6 | Low | Low | Hi | Low | Max: w(vector) = [0 0 1 0] |
| 7 | Low | Low | Low | Hi | Max: w(vector) = [0 0 0 1] |

TABLE 4

More Example Rules for Context Based Aggregation

| Rule | If DCA Index is | If IP Index is | If HLM Index is | If HWM Index is | Then Calculate WLE Index; Max = 1.0 Min = 0.0; If night, then bias = +0.2; If high traffic condition, then bias = +0.2 |
|---|---|---|---|---|---|
| 8 | Low | Low | Low | Low | Mean of 4 Indices: w(vector) = [1 1 1 1] |
| 9 | Low | Hi | Hi | Hi | Mean of 3 of Indices: w(vector) = [0 1 1 1] |
| 10 | Low | Low | Hi | Hi | Mean of 2 Indices: w(vector) = [0 0 1 1] |
| 11 | Hi | Low | Hi | Low | Mean of 2 Indices: w(vector) = [1 0 1 0] |
| 12 | Low | Hi | Low | Hi | Mean of 2 Indices: w(vector) = [0 1 0 1] |
| 13 | Low | Hi | Hi | Low | Mean of 2 Indices: w(vector) = [0 1 1 0] |
| 14 | Hi | Low | Hi | Hi | Mean of 3 of Indices: w(vector) = [1 0 1 1] |
| 15 | Hi | Hi | Low | Hi | Mean of 3 of Indices: w(vector) = [1 1 0 1] |
| 16 | Hi | Low | Low | Hi | Mean of 2 Indices: w(vector) = [1 0 0 1] |

The sub-system 16 may use the techniques described above with reference to the sub-system 14 to aggregate the Rule-Based Index and T Index into the WLE Index. As an example, the WLE Index may be give by:

$$WLE \text{ Index} = \max(T \text{ Index}, \text{Rule Based Index}) \quad (30)$$

Figure 23:
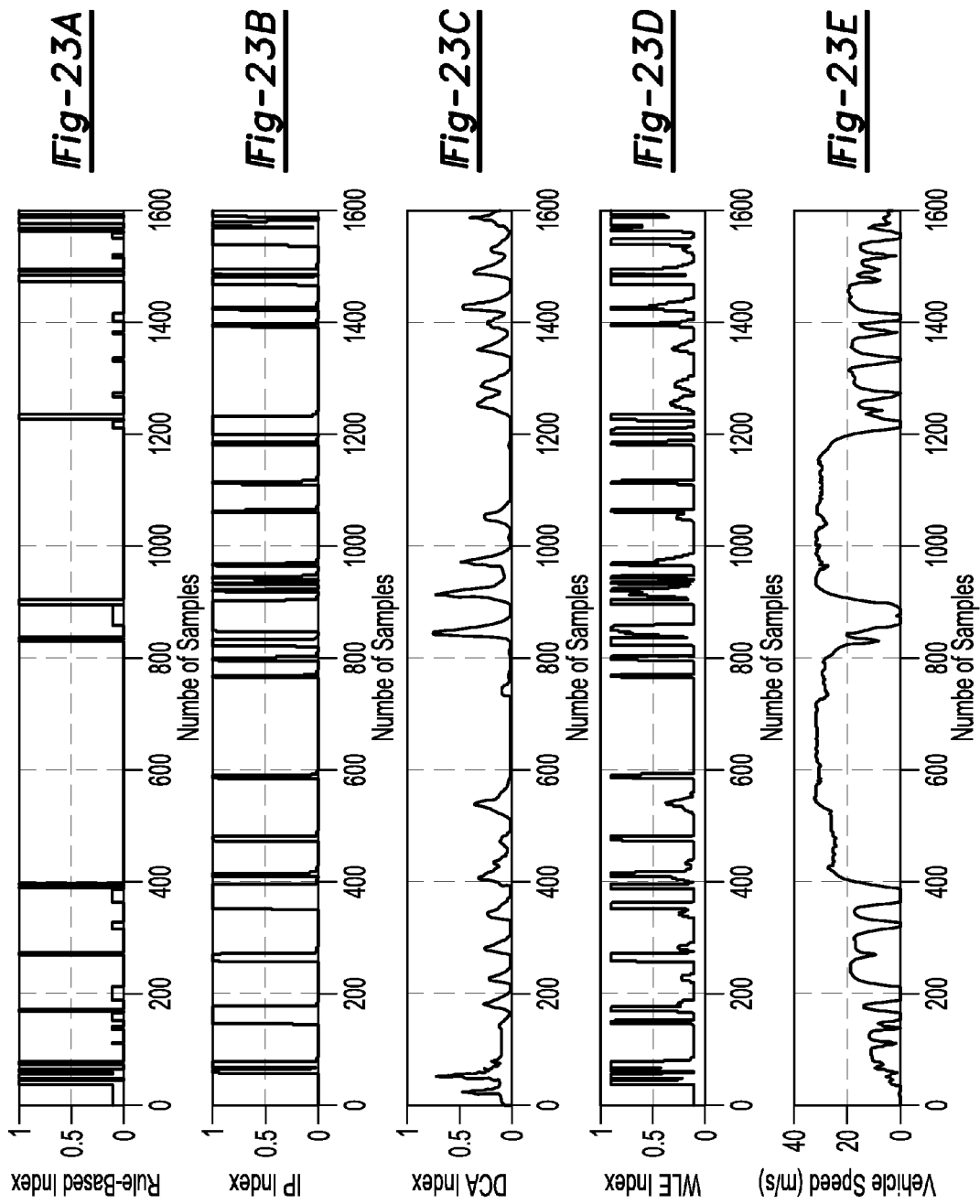
FIGS. 23A through 23E are example plots of a Rule-Based Index, IP Index, DCA Index, composite Workload Estimation (WLE) Index, and vehicle speed respectively.

An example Rule-Based Index, IP Index, and DCA Index are plotted respectively in FIGS. 23A through 23C. These indices have been aggregated using the techniques described herein and plotted in FIG. 23D for conditions where the highest driving demand situations assessed are considered. Vehicle speed is plotted in FIG. 23E for reference.

IX. Long Term Characterization

The WLE Index, in other embodiments, may be characterized over time to provide for HMI recommendations by the sub-system 16 and/or dispatcher 18 (depending on the configuration). Long-term WLE characterization may enable HMI to be tailored to the driver based on the driving demand over time. Consider, for example, that $r_k$ is a variable reflecting the WLE Index value for the driver (at any time instant k). Assume the driving demand is categorized into 3 classes as in {a,b,c} with fuzzy membership functions $\mu_a, \mu_b, \mu_c$ as defined in FIG. 24. Then, the driving behavior, $d_k$, can be inferred from the following example computation $$d_k = [\mu_a(r_k), \mu_b(r_k), \mu_c(r_k)] \quad (31)$$

Figure 24:
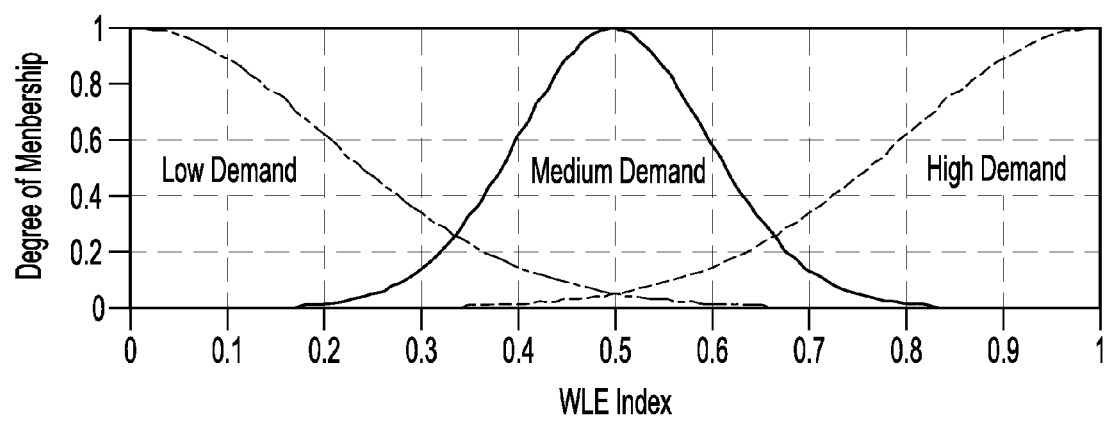
FIG. 24 is an example plot of membership functions for characterizing driver demand based on the WLE Index.

If for example $r_k$ has a value of 0.4, then $d_k$ may be represented as [0.18, 0.62, 0] (according to FIG. 24). The filtered (long term) version of the driving behavior, $d_{f_k}$, can be expressed as in the following $$d_{f_k} = (1-\alpha) d_{f_{k-1}} + \alpha d_k \quad (32)$$

where $\alpha$ is a calibratable forgetting factor (which thus specifies/determines the time period during which the long term version of the driving behavior, $d_{f_k}$, is evaluated). The long-term probability for each of the classes, $(p_k)_i$, may be obtained from $$(p_k)_i = (d_{f_k})_i \left( \sum_{j \in \{a,b,c\}} (d_{f_k})_j \right)^{-1} \quad (33)$$

According to (33), the filtered version of the driving behavior for each of the classes, $(d_{f_k})_i$, is divided by the sum of the filtered version of the driving behavior for all of the classes, $$\left( \sum_{j \in \{a,b,c\}} (d_{f_k})_j \right)^{-1}.$$

If for example $d_{f_k}$ is represented as [0, 0.16, 0.38], then $(p_k)_a$ would be equal to 0 divided by 0+0.16+0.38 $((p_k)_a$ would be equal to 0), $(p_k)_b$ would be equal to 0.16 divided by 0+0.16+0.38 $((p_k)_b$ would be equal to 0.29), and $(p_k)_c$ would be equal to 0.38 divided by 0+0.16+0.38 $((p_k)_c$ would be equal to 0.71).

The final long-term WLE Index characterization of driving demand, $i_k$, may then be inferred from the following $$i_k = \arg\max_{i \in \{a,b,c\}} (p_k)_i \quad (34)$$

Using the example above, the maximum of the $(p_k)_i$ values is 0.71 $((p_k)_c)$. Hence, it may be inferred from (34) that the driving behavior is currently in the "high demand" class.

X. Dispatcher

The dispatcher 18 may apply the computed WLE Index, the long term characterization of the WLE Index, or any one of the DCA Index, IP Index, HL Index, and HW Index (in embodiments where only a single index is used/computed/determined) to modulate the interaction between the infotainment and/or other dialog systems and the driver. The WLE Index provides the estimated workload load used to set/avoid/tailor/limit/schedule voice commands and other tasks to be presented to the driver to improve functionality and safety.

Example interaction with the driver may include generating text-to-speech tell-tales, generating avatar communications, generating notifications regarding in-coming phone calls, generating proactive powertrain commands, generating proactive voice recommendations, generating a tactile response via, for example, a tactile steering wheel, or generating other audio, visual and/or tactile outputs, etc. Each of these example driver interface tasks may have a priority associated with it. For example, generating a notification regarding an in-coming phone call may have a high priority whereas generating a proactive voice recommendation may have a low priority.

Any suitable/known technique may be used to assign a priority type to a given driver interface task. As an example, the dispatcher 18 may implement a high/low priority convention wherein all notifications to be generated regarding in-coming phone calls are assigned a high priority and all vehicle initiated recommendations to be communicated to the driver are assigned a low priority. Other priority schemes, however, may be used. As an example, numbers between 0 and 1.0 may represent the priority of a task: certain tasks may be assigned a priority of 0.3 while other tasks may be assigned a priority of 0.8, etc. In other embodiments, the priority type associated with a driver interface task may be assigned by the controller/processor/subsystem (not shown) that generated the task as known in the art.

Certain embodiments may thus permit a modulated presentation of driver interface tasks based on workload and priority. If for example the WLE Index (or any one of the indices as the case may be) has a value between 0.4 and 0.6, the dispatcher 18 may only allow high priority driver interface tasks to be executed. The dispatcher 18 may schedule lower priority tasks for later execution conditioned upon the WLE Index attaining a value less than 0.4. If for example the WLE Index has a value between 0.7 and 1.0, the dispatcher 18 may prevent all driver interface tasks from being executed. During these periods of high workload, the dispatcher 18 may schedule high priority tasks for later execution conditioned upon the WLE Index attaining a value less than 0.7 and schedule lower priority tasks for later execution conditioned upon the WLE Index attaining a value less than 0.4.

Similarly, if the long term driving behavior is characterized as "high demand," certain/all tasks regardless of their priority may be suspended/delayed/scheduled until the long term driving behavior is characterized as "medium demand" or "low demand." Alternatively, if the long term driving behavior has any probability of being in, for example, the "high demand" class, certain/all tasks may be suspended/delayed/scheduled until the probability of being in "high demand" is zero. Other scenarios are, of course, also possible. In embodiments where a priority type is not used to categorize tasks for example, all tasks may be suspended/delayed/scheduled depending on the inferred workload.

In the case of an in-coming phone call received during periods of high workload, the dispatcher 18 may put the call through to a voice mail system. Once the WLE Index has attained an appropriate value, the dispatcher 18 may generate a notification indicating that a call was received.

The algorithms disclosed herein may be deliverable to a processing device, such as any/all of the systems 12, 13, 14, 16, 18, which may include any existing electronic control unit or dedicated electronic control unit, in many forms including, but not limited to, information permanently stored on non-writable storage media such as ROM devices and information alterably stored on writeable storage media such as floppy disks, magnetic tapes, CDs, RAM devices, and other magnetic and optical media. The algorithms may also be implemented in a software executable object. Alternatively, the algorithms may be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While embodiments of the invention have been illustrated and described, it is not intended that these embodiments illustrate and describe all possible forms of the invention. The words used in the specification are words of description rather than limitation, and it is understood that various changes may be made without departing from the spirit and scope of the invention.

What is claimed:

1. A driver interface system for a vehicle comprising:
a system configured to generate tasks; and
a processor programmed to (i) monitor over time an activity level of a driver, (ii) determine a variability of the activity level relative to a mean value of the activity level for the driver according to a recursive computation of a determinant of a covariance of the activity level, (iii) determine a driver workload based on the variability, (iv) receive a plurality of driver interface tasks to be executed, and (v) selectively delay or prevent at least some of the plurality of driver interface tasks from being executed based on the driver workload.

2. The system of claim 1 wherein the at least one processor is further programmed to recursively calculate a variance of a unit dimensional signal to determine the variability of the activity level.

3. The system of claim 1 wherein the activity level is based on driver heart-rate information.

4. The system of claim 1 wherein the activity level is based on driver respiration information.

5. The system of claim 1 wherein the activity level is based on driver galvanic skin response information.

6. The system of claim 1 wherein the activity level is based on driver eye-gaze information.

7. The system of claim 1 wherein the activity level is based on driver head pose information.

8. The system of claim 1 wherein each of the plurality of driver interface tasks includes a priority type and wherein the at least one processor is further programmed to selectively delay or prevent at least some of the plurality of driver interface tasks from being executed further based on the priority type.

9. The system of claim 1 wherein the plurality of driver interface tasks includes at least one of generating an audio output, generating a visual output, and generating a tactile output.

10. A method for managing interface tasks comprising:
determining a variability of a monitored driver activity level relative to a mean value of the driver activity level according to a recursive computation of a determinant of a covariance of the driver activity level;
receiving a plurality of interface tasks to be executed; and
selectively delaying or preventing at least some of the plurality of interface tasks from being executed based on the variability.

11. The method of claim 10 wherein determining the variability of the driver activity level includes recursively calculating a variance of a unit dimensional signal.

12. The method of claim 10 wherein the driver activity level is based on driver heart-rate information.

13. The method of claim 10 wherein the driver activity level is based on driver respiration information.

14. The method of claim 10 wherein the driver activity level is based on driver eye-gaze information.

15. The method of claim 10 wherein the driver activity level is based on driver head pose information.

16. The method of claim 10 wherein each of the plurality of interface tasks includes a priority type and wherein at least some of the plurality of interface tasks are selectively delayed or prevented from being executed further based on the priority type.

17. The method of claim 10 wherein the plurality of interface tasks includes generating a notification regarding an in-coming call and wherein selectively delaying or preventing at least some of the plurality of interface tasks from being executed based on the variability includes forwarding the in-coming call to a voice mail system.

18. The method of claim 10 wherein the plurality of interface tasks includes at least one of generating an audio output, generating a visual output, and generating a tactile output.

* * * * *